United States Patent [19]
Gelboin et al.

[11] Patent Number: 5,939,530
[45] Date of Patent: Aug. 17, 1999

[54] INHIBITORY AND NON-INHIBITORY ANTIGEN BINDING POLYPEPTIDES AGAINST HUMAN P450 ENZYMES

[75] Inventors: Harry V. Gelboin, Chevy Chase; Frank J. Gonzalez, Bethesda, both of Md.

[73] Assignee: The United States of America as represented by the Department of Health and Human Services, Washington, D.C.

[21] Appl. No.: 08/559,808

[22] Filed: Nov. 17, 1995

[51] Int. Cl.$^6$ ............................... C07K 16/00; C12P 21/08
[52] U.S. Cl. .................................. 530/387.1; 530/387.3; 530/388.1; 530/388.26; 530/388.85
[58] Field of Search ........................... 530/388.26, 387.1, 530/387.3, 387.9, 388.15, 388.1, 388.85; 435/69.6

[56] References Cited

U.S. PATENT DOCUMENTS 4,946,778   8/1990   Ladner et al. .......................... 435/69.6

OTHER PUBLICATIONS

Kerr et al (Pharm Res, 1991, 8 No. 10 Suppl. S239).
Christians et al (Ther. Drug. Monit, 1993, 15#2, 145).
Ohmori et a (Biol. Pharm. Bull, 1993, 16:571–575).
Yon et al (Anesthesiology, 1992, 77:467–474).
Patten et al (Chem. Res. Toxicol, 1993, 6:511–518.
Gillam et al (Arch. Biochem & Biophys, 1994, 312;59–66).
Aoyama et al, Endocrinology,126: 3101,–3106(1990).
Harlow & Lane, Antibodies, Cold Spring Harbor Laboratory 1988, p. 141.
Francois Berthou et al., "Involvement of Cytochrome P450 3A Enzyme Family in the Major Metabolic Pathways of Toremifene in Human Liver Microsomes," *Biochemical Pharmacology*, 1994, vol. 47, No. 10, London, GB, pp. 1883–1895.
Thomas K. H. Chang et al., "Differential Activation of Cyclophosphamide and Ifosphamide by Cytochromes P–450 2B and 3A in Human Liver Microsomes," *Cancer Research*, Dec. 1, 1993, vol. 53, No. 23, CNREA 8, Baltimore, MD, USA, pp. 5629–5637.
Harry V. Gelboin et al., "Inhibitory and Non–Inhibitory Monoclonal Antibodies to Human Cytochrome P450 3A3/4," *Biochemical Pharmacology*, vol. 50, No. 11, 1995, London, GB, pp. 1841–1850.
Harry V. Gelboin et al., "Inhibitory and Non–Inhibitory Monoclonal Antibodies to Human Cytochrome P450 2E1," *Chemical Research in Toxicology*, Sep. 1996, vol. 9, No. 6, CRTOEC 9 (6) 917–1056 (1196), London, GB, pp. 1023–1030.
James W. Harris et al., "Metabolism of Taxol by Human Hepatic Microsomes and Liver Slices: Participation of Cytochrome P450 3A4 and an Unknown P450 Enzyme$^{1,2}$," *Cancer Research*, Aug. 1, 1994, vol. 54, No. 15, CNREA 8, Baltimore, MD, USA, pp. 4026–4035.
Clyde W. Wheeler et al., "Detection of Human Lung Cytochromes p450 That Are Immunochemically Related to Cytochrome P450IIE1 and Cytochrome P450IIIA," *Biochemical Pharmacology*, Jul. 7, 1992, vol. 44, No. 1, London, GB, pp. 183–186.
Guengerich et al., Chem. Res. Toxicol 4: 168–179 (1991).
Guengerich et al., Assessment of the Use of Single Cytochrome P450 Enzymes in Drug Research, pp.161–186 (Springer Verlag 1994).
Park et al., Biochemical Pharmacology 35(17): 2859–2867 (1986).
Ladona et al., Biochemical Pharmacology 37(24): 4735–4741 (1988).
Barnes et al., Biochem. J. 248: 301–304 (1987).
Beaune et al., Biochemical Pharmacology 34(19): 3547–3552 (1985).
Ko et al., Cancer Research 47: 3101–3109 (Jun. 15, 1987).
Buters et al., Drug Metabolism & Disposition 22(5): 688–692 (1994).
Gelboin, Pharmacological Reviews 45(4):413–453 (1993).

*Primary Examiner*—Paula K. Hutzell
*Assistant Examiner*—Susan Ungar
*Attorney, Agent, or Firm*—Townsend and Townsend and Crew, LLP

[57] ABSTRACT

Antigen binding polypeptides that specifically bind human cytochrome P450 3A3, 3A4, and 3A5 and that specifically inhibit the enzyme activity of human cytochrome P450 3A3, 3A4, and 3A5 are described. Antigen binding polypeptides that specifically bind to human cytochrome P450 3A3 and 3A4 are also described. Antigen binding polypeptides which specifically bind to human cytochrome P450 2E1 and which specifically inhibit the enzyme activity of human cytochrome P450 2E1 are described. Antigen binding polypeptides which specifically bind to human cytochrome P450 2E1 are also described. Methods of determining the contribution of human cytochrome P450s to the metabolism of compounds, using the antigen binding polypeptides of the invention, are also described.

14 Claims, 7 Drawing Sheets

INHIBITORY AND NON-INHIBITORY ANTIGEN BINDING POLYPEPTIDES AGAINST HUMAN P450 ENZYMES

BACKGROUND OF THE INVENTION

The cytochrome P450 enzymes (P450s) play an important role in metabolizing xenobiotics and certain endobiotics. The P450s exist in multiple isozymic forms which direct the metabolic flow of individual substrates. Gelboin, *Pharmacol. Rev.* 45: 413 (1993). Compounds which are metabolized by the cytochrome P450 enzymes include various drugs, carcinogens, mutagens, pesticides, steroids, fatty acids, bile acids and prostaglandins. Gonzalez, loc. cit. 40: 243 (1989). Cytochrome P450 metabolism of xenobiotics can result in detoxification of toxic compounds by their conjugation into excretable forms or can result in activation of compounds into metabolites that are toxic, mutagenic, or carcinogenic. Many steroids are deactivated by cytochrome P450-catalyzed oxidation.

The human cytochrome P450 3A family consists of several isozymes. Cytochome P450 3A4 is the most abundant of the P450 3A enzymes in the human liver, but its expression levels in the liver and other tissues vary. Enzymatically active human P450 3A4 has been produced from cloned cDNA expressed in a baculovirus expression system. Buters et al., *Drug Metab. Dispos.* 22: 688 (1994). The nucleotide sequence of cytochrome P450 3A3 is 98% identical to the P450 3A4 nucleotide sequence. Guengerich et al., "The Importance of Cytochrome P450 3A Enzymes in Drug Metabolism," in ASSESSMENT OF THE USE OF SINGLE CYTOCHROME P450 ENZYMES IN DRUG RESEARCH 161–186 (Springer Verlag 1994). P450 3A3 has been cloned and expressed, and its enzyme activity is nearly identical to that of 3A4. Schuetz, et al., *Hepatology*, 18:1254–62, 1993; Molowa, et al., *Proc. Natl. Acad. Sci. U.S.A.* 83:5311–5315, 1986. Some researchers believe that 3A3 is in fact 3A4 and the minor sequence variations between 3A3 and 3A4 are due to sequencing errors. 3A3 and 3A4 will be referred to separately throughout the specification, with the recognition that further research may demonstrate these two enzymes to actually be the same. Approximately one fourth of individuals have the P450 3A5 enzyme, and when expressed in the liver, its level is lower than that of the P450 3A4 enzyme. Id. P450 3A5 has not been characterized as well as the 3A4 enzyme. It has been shown that P450 3A5 and 3A4 have similar, but not identical, substrate specificities. Id.

Cytochrome P450 3A4 and 3A3 are very important members of the P450 class of enzymes. The human P450 3A4 and 3A3 assume an especially important place among the human P450s because they metabolize a large variety of drugs, steroids and carcinogens. Id. Cytochromes P450 3A3 and 3A4 are considered the most important P450s for a wide range of high molecular weight substrates which include many of the known clinically useful drugs, such as tranquilizers, anti-depressants, immunosuppressants and anti-cancer drugs. A partial list of the P450 3A substrates appears in Table 1 below.

TABLE 1

| P450 3A SUBSTRATES | | |
|---|---|---|
| epipodophyllotoxins | sulfoxide | tamoxifen |
| cyclosporin | teniposide | (S)-warfarin |
| erythromycin | etoposide | α-naphthoflavone |
| benzphetamine | midazolam | phenanthrene |

TABLE 1-continued

| P450 3A SUBSTRATES | | |
|---|---|---|
| triacetyloleandomycin | taxol | benzo[a]pyrene |
| nifedipine | FL-506 | sulfentamil |
| cocaine | vinblastine | codeine |
| cortisol | afentanil | imipramine |
| testosterone | vindesine | dapsone |
| aflatoxin B1 | amiodarone | aminochrysene |
| lidocaine | mephenytoin | 1-nitropyrene |
| amphetamine | digitoxin | alfentanil |
| benzo[a]pyrene 7, 8-diol | | |

Cytochrome P450 2E1 plays a major role in the metabolism of a variety of low molecular weight compounds including environmental chemicals, and carcinogens such as short-chain dialkylnitrosamines, benzene, styrene, halomethanes, vinyl halides, ethyl carbamate, and small vinyl monomers. Guengerich et al., *Chem. Res. Toxicol.* 4: 168 (1991). The human 2E1 also metabolizes clinically useful drugs such as the anesthetic chlorzoxazone and the analgesic acetaminophen as well as caffeine. The rat 2E1 nucleotide sequence is 75% homologous to the human 2E1 and the amino acid sequences of rat and human are 78% homologous. See Song, et al. *J. Biol. Chem.*, 261:16689–16697, 1986. A partial list of the P450 2E1 substrates appears in Table 2.

TABLE 2

| SUBSTRATES FOR 2E1 | |
|---|---|
| Chlorzoxazone | vinyl bromide |
| Acetaminophen | vinyl carbamate |
| Acrylonitrile | ethyl carbamate |
| p-Nitrophenol | CC14 |
| N-Nitrosodimethylamine (NDMA) | CHC13 |
| N-Nitrodiethylamine (NDEA) | 1, 2-Dichloropropane |
| Enflurane | CH3CC13 |
| N-Nitrosonornicotine (NNN) | Tricholordethylene |
| 1, 1-Dimethylformamide | Benzene |
| Stryrene | Eicosatetraenoic acid |
| Caffeine | N, N-Dimethylformamide |
| 1, 3-Butadiene | Ethylene dibromide |
| Furan | Ethylene dichloride |
| p-Nitroanisole | vinyl chloride |
| Sevoflurane, Isoflurane & Methoxyflurane | |
| 1, 1, 2, 2-Tetrafluoro-1-(2, 2, 2-trifluoroethoxy)-ethane (HFE) | |

Many current methods for assessing the contribution of specific P450 enzymes to the metabolism of various chemicals are not effective. Chemical enzyme inhibitors are non-specific. Comparison of metabolism rates in different tissue preparations is not useful because this method does not distinguish between P450 isozymes. Reconstitution of catalytic activities using purified enzyme preparations does not provide information about enzyme activity in vivo. Inhibition of enzyme activity with antibodies to cytochrome P450s has also been reported, see Guengerich et al. (1991), supra, but the production of monoclonal antibodies to human P450s has been greatly hindered by the inability to obtain human P450s in amounts sufficient for immunization. Barnes et al. reported monoclonal antibodies made against human liver microsomes or semi-purified human P450s. These antibodies recognized a 53 kDa band on a Western blot, but there was no characterization of whether these antibodies recognize 3A3, 3A4, 3A5 or other human P450s. In addition, there was no investigation of inhibition of cytochrome P450 enzyme activity by these antibodies. Barnes et al., *Proc. Nat'l Acad. Sci. USA* 84: 4073 (1987).

Beaune et al. obtained monoclonal antibodies against a mixture of purified human P450s, but the precise identity of the P450 isozymes with which these antibodies cross react is unclear. This report also did not discuss antibody inhibition of enzyme activity. Beaune et al., *Biochem. Pharmacol.* 34: 3547 (1985). Park et al., "Preparation and characterization of monoclonal antibodies to pregnenolone 16-α-carbonitrile inducible rat liver cytochrome P450," *Biochem. Pharmacol.* 35: 2859 (1986), reported monoclonal antibodies against rat P450 3A1/2. The structure and function of the rat 3A1/2 enzymes are similar, but not identical to the human P450 3A3 or 3A4 enzymes. Park et al. did not investigate antibody-mediated inhibition of rat 3A1/2 enzyme activity.

Guengerich et al., *Chem. Res. Toxicol.* 4: 168 (1991), reported on a polyclonal antibody against human P450 2E1 which inhibited the metabolism of 2E1 substrates in human liver microsomes. A monoclonal antibody against rat cytochrome P450 2E1 was prepared by Ko et al., *Cancer Res.* 47: 3101 (1987), and was found to inhibit P450 2E1-mediated metabolism of certain chemicals in rat microsomes. Ko et al. also isolated a monoclonal antibody against rat P450 2E1 which recognized P450 2E1 on a Western blot but did not inhibit enzyme activity.

Cytochrome P450s are a paradigm for multi-isozymic systems whose activity may result in metabolic products with opposing physiological and pathological consequences. The large multiplicity of P450 forms, their differing structure and function, their often poorly defined substrate and product specificity, and their heterogeneous distribution in vivo make difficult the determination of the quantitative contribution of each P450 to the metabolism of specific substrates.

A need therefore exists for reagents that can identify and inhibit certain human cytochrome P450 enzymes specifically. A thorough understanding of the different P450 isozymes, their specificity, regulation, and distribution is crucial to designing more effective drugs, evaluating the modes of action of drugs, carcinogens and environmental chemicals, and developing inhibitors of carcinogens and other toxic chemicals. Individuals sensitive to particular chemicals could be characterized based on their cytochrome P450 makeup, permitting administration of the most effective drugs and toxicity inhibitors. Monoclonal antibodies which inhibit cytochrome P450 3A3, 3A4, and 3A5 and P450 2E1 would be powerful analytical tools because the cytochrome P450 3A enzymes play an important role in metabolizing a wide variety of xenobiotics and endobiotics, including many large molecular weight compounds, and P450 2E1 plays an important role in metabolizing many small molecular weight chemicals and carcinogens. In order to produce specific monoclonal antibodies, there must be a large enough supply of purified cytochrome P450s to immunize for the production of antibodies.

SUMMARY OF THE INVENTION

It therefore is an object of the present invention to provide reagents which can specifically identify and inhibit human cytochrome P450 3A3, 3A4 and 3A5 and to provide reagents which can specifically identify and inhibit human cytochrome P450 2E1.

It is also an object of the invention to provide monoclonal antibodies and other antigen binding polypeptides which can specifically identify and inhibit human P450 3A3, 3A4, and 3A5 and human P450 2E1.

It is a further object of the invention to provide methods utilizing antigen binding polypeptides that can determine the contribution of human P450 3A3, 3A4, 3A5 and 2E1 to the metabolism of xenobiotics and endobiotics in samples comprising one or more human cytochrome P450 enzymes and in samples of various cells, microsomes, and tissues.

Thus, the invention relates to antigen binding polypeptides that specifically bind to human cytochrome P450 3A3, 3A4 and 3A5, and that specifically inhibit the enzyme activity of human cytochrome P450 3A3, 3A4 and 3A5. The invention also relates to antigen binding polypeptides that specifically bind to human cytochrome P450 2E1, and that specifically inhibit the enzyme activity of human cytochrome P450 2E1. The invention also relates to antigen binding polypeptides that specifically bind to human cytochrome P450 3A3 and 3A4. The invention further relates to antigen binding polypeptides that specifically bind to human cytochrome P450 2E1. These antigen binding polypeptides of the invention include monoclonal antibodies, antibody fragments and single chain antigen binding polypeptides with the P450-recognition properties described above.

The invention further relates to a method for determining the contribution of human cytochrome P450 3A3, 3A4, or 3A5 to the metabolism of a compound, comprising the steps of:

(a) contacting one or more samples comprising human cytochrome P450 3A3, 3A4, 3A5, or any combination thereof, with
  (i) varying amounts of an antigen binding polypeptide of the invention that specifically binds to human cytochrome P450 3A3, 3A4 and 3A5, and that specifically inhibits the enzyme activity of human cytochrome P450 3A3, 3A4 and 3A5; and
  (ii) said compound; and then
(b) measuring the metabolism of said compound by the one or more samples of step (a), whereby the contribution of cytochrome P450 3A3, 3A4, or 3A5 to the metabolism of said compound is proportional to the inhibition of said metabolism by said antigen binding polypeptide.

The invention further relates to a method for determining the contribution of cytochrome P450 3A3, 3A4, and 3A5 to the metabolism of a compound by mammalian cells, microsomes, or tissue, comprising the steps of:

(a) contacting one or more samples comprising mammalian cells, microsomes, or tissue with
  (i) varying amounts of an antigen binding polypeptide of the invention that specifically binds to human cytochrome P450 3A3, 3A4 and 3A5, and that specifically inhibits the enzyme activity of human cytochrome P450 3A3, 3A4 and 3A5; and
  (ii) said compound; and then
(b) measuring the metabolism of said compound by the one or more samples of step (a), whereby the contribution of cytochrome P450 3A3, 3A4, or 3A5 to the metabolism of said compound by mammalian cells, microsomes, or tissue is proportional to the inhibition of said metabolism by said antigen binding polypeptide.

The invention further relates to a method for determining the contribution of human cytochrome P450 2E1 to the metabolism of a compound, comprising the steps of:

(a) contacting one or more samples comprising cytochrome P450 2E1 with
  (i) varying amounts of an antigen binding polypeptide of the invention that specifically binds to human cytochrome P450 2E1, and that specifically inhibits the enzyme activity of human cytochrome P450 2E1; and (ii) said compound; and then (b) measuring the metabolism of said compound by the one or more samples of step (a), whereby the contribution of human cytochrome P450 2E1 to the metabolism of said compound is proportional to the inhibition of said metabolism by said antigen binding polypeptide.

The invention further relates to a method for determining the contribution of cytochrome P450 2E1 to the metabolism of a compound by mammalian cells, microsomes, or tissue, comprising the steps of:

(a) contacting one or more samples of cells, microsomes, or tissue with
  (i) varying amounts of an antigen binding polypeptide of the invention that specifically binds to human cytochrome P450 2E1, and that specifically inhibits the enzyme activity of human cytochrome P450 2E1; and
  (ii) said compound; and then
(b) measuring the metabolism of said compound by the one or more samples in step (a), whereby the contribution of human cytochrome P450 2E1 to the metabolism of said compound by mammalian cells, microsomes, or tissue is proportional to the inhibition of said metabolism by said antigen binding polypeptide.

DETAILED DESCRIPTION OF PREFERRED EMBODIMENTS

Figure 1:
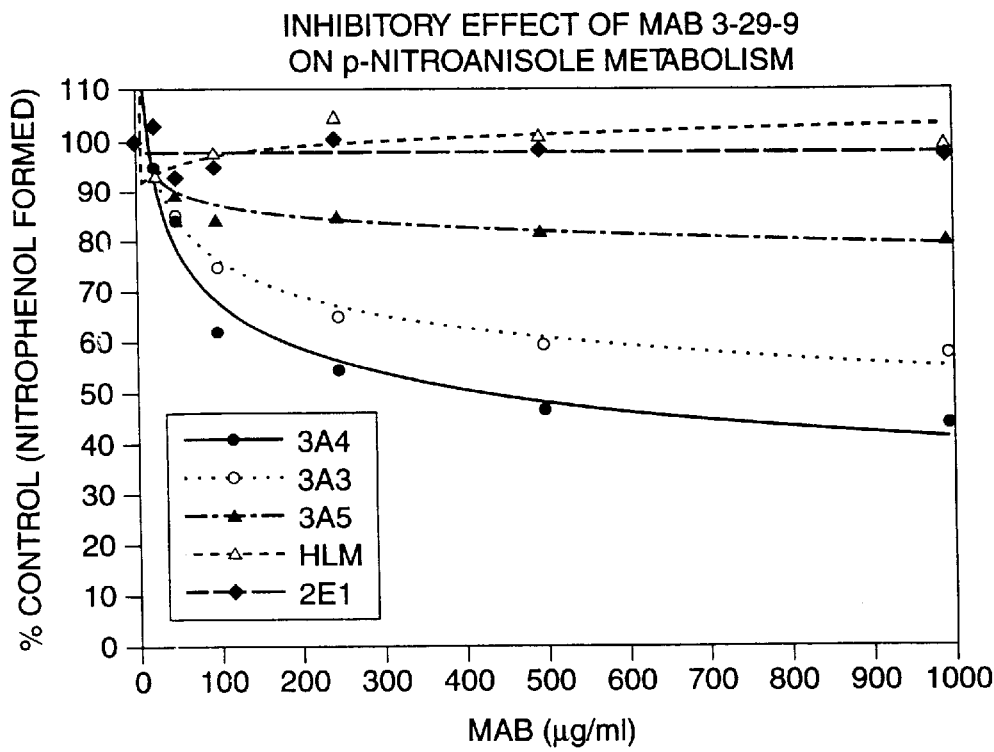
FIG. 1 shows the inhibitory effect of monoclonal antibody 3-29-9 on p-nitroanisole metabolism. Monoclonal antibody 3-29-9 and P450 were pre-incubated at 37° C. for 5 minutes and diluted with KPi buffer. Incubations were carried out for 20 min and terminated with dichloromethane (DCM). An internal standard, 4-nitrophenol was added. Nitrophenol (DO) and 4-nitrophenol were derivatized for gas chromatography-mass spectroscopy. Percentage of control in the formation of nitrophenol by 3A3, 3A4, 3A5 in human livery microsomes (HLM), and dexamethasane-induced rat liver microsomes (RLM) is expressed as [(metabolite formed/internal standard) with 3-29-9]/[(metabolite formed/internal standard) without 3-29-9].

The present inventors have determined that, by using recombinantly produced human cytochrome P450 3A4 and 2E1, a monoclonal antibody can be produced that specifically inhibits the enzyme activity of human cytochrome P450 3A3, 3A4, and 3A5, and also that a monoclonal antibody can be produced that specifically inhibits the enzyme activity of human cytochrome P450 2E1. Monoclonal antibodies which specifically inhibit these human enzyme activities have not been isolated previously; nor has there been any indication that such specific inhibition was attainable. By the same token, it also has been discovered that a monoclonal antibody which specifically binds to human P450 3A3 and 3A4 but not to 3A5 can be produced, as can a monoclonal antibody that specifically binds to human P450 2E1. Again, these binding specificities were not presaged by any structure/function relationship or other information available heretofore.

Based on knowledge concerning these monoclonal antibodies, it also is possible to prepare a range of antigen binding polypeptides that possess the characteristic, highly desirable P450-recognition properties described above. Examples of antigen binding polypeptides of the invention include (A) a "half antibody" molecule, i.e., a single heavy:light chain pair, and (B) an antibody fragment, such as the univalent fragments Fab and Fab', the divalent fragment F(ab')$_2$, and a single or double chain Fv fragment. A fragment of the present invention possesses the characteristic specificity of one of the aforementioned monoclonal antibodies; that is, for binding human P450 3A3, 3A4 and 3A5 (antibody 3-29-9), for human 3A3 and 3A4 (antibody 275-1-2), for binding human 2E1 (antibody 1-73-18), or for binding human 2E1 (antibody 2-106-12).

Also illustrative of an antigen binding polypeptide within the present invention is a non-peptide "mimetic," i.e., a compound that mimics an epitope binding site of 3-29-9 or 275-1-2 or 1-73-18 or 2-106-12, but that is water-soluble, resistant to proteolysis, and non-immunogenic. Conformationally restricted, cyclic organic peptides which mimic any of these antibodies can be produced in accordance with known methods described, for example, by Saragovi, et al., *Science* 253: 792 (1991).

In accordance with the present invention, fragments within the invention can be obtained from a monoclonal antibody, produced as described above, by methods that include digestion with enzymes such as pepsin or papain and/or cleavage of disulfide bonds by chemical reduction. Alternatively, monoclonal antibody fragments encompassed by the present invention can be synthesized using an automated peptide synthesizer such as those supplied commercially by Applied Biosystems, Multiple Peptide Systems and others, or they may be produced manually, using techniques well known in the art. See Geysen et al., *J. Immunol. Methods* 102: 259 (1978). Direct determination of the amino acid, sequences of the variable regions of the heavy and light chains of the monoclonal antibodies according to the invention can be carried out using conventional techniques.

As noted, a fragment according to the present invention can be an Fv fragment. An Fv fragment of an antibody is made up of the variable region of the heavy chain (Vh) of an antibody and the variable region of the light chain of an antibody (Vl). Proteolytic cleavage of an antibody can produce double chain Fv fragments in which the Vh and Vl regions remain non-covalently associated and retain antigen binding capacity.

Double chain Fv fragments also can be produced by recombinant expression methods well known in the art. See Skerra et al., *Science* 240: 1038 (1988), and King et al., *Biochemical J.* 290: 723 (1991). Briefly, the amino acid sequence of the variable regions of the heavy and light chains of the monoclonal antibodies according to the invention can be obtained by direct amino acid sequencing using methods well known to those in the art. From this amino acid sequence, synthetic genes can be designed which code for these variable regions and they can both be inserted into an expression vector. Two polypeptides can be expressed simultaneously from a mammalian or bacterial host, resulting in formation of an active Fv fragment.

An antigen binding polypeptide of the present invention also can be a single-chain molecule or so-called "single chain antigen binding polypeptide," a phrase used in this description to denote a linear polypeptide that binds antigen with specificity and that comprises variable or hypervariable regions from the heavy and light chain chains of an antibody. Single chain antigen binding polypeptides that retain an antigen-binding capacity that is characteristic of the present invention can be produced by conventional methodology. The Vh and Vl regions of the Fv fragment can be covalently joined and stabilized by the insertion of a disulfide bond. See Glockshuber, et al., *Biochemistry* 1362 (1990). Alternatively, the Vh and Vl regions can be joined by the insertion of a peptide linker. A gene encoding the Vh, Vl and peptide linker sequences can be constructed and expressed using a recombinant expression vector. See Colcher, et al., *J. Nat'l Cancer Inst.* 82: 1191 (1990). Amino acid sequences comprising hypervariable regions from the Vh and Vl antibody chains can also be constructed using disulfide bonds or peptide linkers, as described herein.

In one aspect, therefore, the present invention relates to monoclonal antibodies and fragments thereof that specifically, inhibit the enzyme activity of human cytochrome P450 3A3, 3A4 and 3A5, and to monoclonal antibodies or fragments that specifically inhibit the enzyme activity of human cytochrome P450 2E1. The invention also relates to monoclonal antibodies that specifically bind to human P450 3A3 and 3A4 and which bind to human P450 2E1. An example of the antibodies contemplated by the present invention is a monoclonal antibody, designated "3-29-9," that inhibits the activity of human cytochrome P450 3A3, 3A4 and 3A5, and that has been deposited at the American Tissue Type Culture Collection (ATCC) under accession number 97337. Another example of an antibody contemplated by the present invention is the monoclonal antibody 1-73-18, which inhibits the activity of human cytochrome P450 2E1, and which has been deposited under ATCC accession number 97339. A further example of the antibodies contemplated by the present invention is the monoclonal antibody 275-1-2, which specifically binds to cytochrome P450 3A3 and 3A4; 275-1-2 has been deposited under ATCC accession number 97338. Still another example of the antibodies of the present invention is the monoclonal antibody 2-106-12, which specifically binds to cytochrome P450 2E1, having been deposited under ATCC accession number 97340. The address of the ATCC is 12301 Parklawn Dr., Rockville Md. 20852, USA. All of the antibodies were deposited on Nov. 16, 1995.

Monoclonal antibody 3-29-9 is specific for human cytochrome P450 3A3, 3A4, and 3A5 because it does not cross react with other recombinantly-expressed human P450s and does not cross react with various recombinantly-expressed rat and mouse cytochrome P450s. Similarly, monoclonal antibody 275-1-2 is specific for P450 3A3 and 3A4 and does not cross react with other recombinantly-expressed human, rat or mouse P450s. Monoclonal antibody 2-106-12 is specific for cytochrome P450 2E1, in that it does not cross react with various other recombinantly-expressed human P450s, nor does it react with recombinantly-expressed rat or mouse P450s. Monoclonal antibody 1-73-18 is also specific for P450 2E1 because it does not cross react with various recombinantly-expressed human, rat and mouse P450s. The present inventors have discovered that monoclonal antibody 3-29-9 strongly inhibits the enzyme activity of human cytochrome P450 3A, 3A4 and 3A5, and that monoclonal antibody 1-73-18 strongly inhibits cytochrome human P450 2E1 activity.

Antibody 3-29-9 inhibited the metabolism of phenanthrene by purified P450 3A3, 3A4 and 3A5 and human liver microsomes. Antibody 3-29-9 did not inhibit metabolism of phenanthrene by rat liver microsomes. Antibody 3-29-9 inhibited the metabolism of diazepam by purified 3A3, 3A4 and 3A5 and also inhibited diazepam metabolism by human liver microsomes. Antibody 3-29-9 did not inhibit metabolism of diazepam by rat liver microsomes. Taxol metabolism by purified P450 3A3 and 3A4 and by human liver microsomes was inhibited by antibody 3-29-9. Metabolism of taxol by rat liver microsomes was not affected by antibody 3-29-9. The metabolism of cyclosporin by purified 3A4 was inhibited by antibody 3-29-9. The metabolism of testosterone by purified P450 3A3, 3A4, 3A5, and by human liver microsomes was inhibited by antibody 3-29-9. The metabolism of p-nitroanisole by 3A3, 4 and 5 was inhibited by antibody 3-29-9, but the inhibition was moderate. But p-nitroanisole is considered a poor substrate for P450 3A3 and 3A4.

The antigen binding polypeptides according to this invention include any polypeptide, natural or synthetic, that has the binding specificity of monoclonal antibody 3-29-9, 1-73-18, 275-1-1 or 2-106-12. One antigen binding polypeptide according to the invention binds to an epitope on human P450 3A3, 3A4 and 3A5 and specifically inhibits the enzyme activity of human P450 3A3, 3A4, and 3A5. Another antigen binding polypeptide according to the invention binds to an epitope on human P450 2E1 and specifically inhibits human P450 2E1 enzyme activity. Another antigen binding polypeptide according to the invention specifically binds to an epitope on human P450 3A3 and 3A4. Still another antigen binding polypeptide according to the invention binds to an epitope on P450 2E1.

Preferably, an antigen binding polypeptide of the present invention binds to P450 3A3, 3A4 and 3A5 in such a way as to inhibit the enzyme activity of P450 3A3, 3A4, and 3A5. Preferably another antigen binding polypeptide according to the invention binds to P450 2E1 in such a way as to inhibit the enzyme activity of P450 2E1. Preferably other antigen binding polypeptides of the invention bind to human P450 3A3 and 3A4 or 2E1, but do not inhibit P450 enzyme activity.

Monoclonal antibodies can be produced in various ways using techniques well understood by those having ordinary skill in the art. Details of these techniques are described in ANTIBODIES: A LABORATORY MANUAL 726, Cold Spring Harbor Publications (1988). The production of quantities of recombinant human P450 3A4 sufficient for immunization can be carried out using a recombinant expression system, such as the baculovirus system used to express human P450 3A4, which is described in Buters et al., *Drug Metab. Dispos.* 22: 688 (1994). This publication also describes purification procedures for the recombinantly-produced human P450 3A4. The production of quantities of recombinant human P450 2E1 sufficient for immunization can be carried out using a recombinant expression system, such as the baculovirus system. Construction of baculovirus containing the human P450 2E1 gene is described in Gonzalez, et al., Meth. Enzymol., 206:93–99, 1991. *Spodoptera frugiperda* or Trichoplusia cells can be transformed with this baculovirus and 72–96 hours after infection 2E1 protein can be harvested. Transformed cells can be sonicated, centrifuged, and resuspended in buffer containing sodium cholate. Following stirring of the suspension, it can be further centrifuged, resuspended in buffer, and dialyzed to remove excess sodium cholate. FPLC chromatography using an octyl sepharose column can be used as the initial 2E1 purification step. Those fractions absorbing light at 405 nm can be pooled, dialyzed and loaded onto an HPLC hydroxyapatite column. Protein samples eluted from this column can be further subjected to artificial membrane chromatography using the techniques described in Pidgeon, et al., Anal. Biochem. 194:163–173, 1991. Following rechromatography on an HPLC hydroxapatite column, samples of 2E1 can be further centrifuged to remove precipitates. See Laethem, et al., J. Biol. Chem. 268:12912 (1993).

Generally, monoclonal antibodies according to the present invention are prepared by immunizing BALB/c mice intraperitoneally with purified recombinantly expressed P450 3A4 or P450 2E1 with a series of booster immunizations. Several days after the final immunization, a mouse is sacrificed, its spleen removed and the spleen cells are fused with myeloma cells. Hybrids are screened using a solid phase enzyme-linked immunosorbent assay and P450 3A4 or P450 2E1 as antigen. Antibody-positive wells are re-screened and those hybridomas of interest are cloned at least three times.

In another preferred embodiment, the present invention relates to a method of determining the contribution of human P450 3A3, 3A4 and 3A5 to the metabolism of compounds. "Compound" is used here to denote any xenobiotic, such as a drug, carcinogen, pesticide or other industrial or environmental chemical, or any endobiotic, such as a steroid hormone. The term "metabolism" is used to indicate the processing a compound into a metabolite or metabolites by the action of an enzyme or enzymes, where the chemical structure of the metabolite(s) is different from the compound prior to its metabolism. As noted, human P450 3A3 and 3A4 are responsible for the metabolism of a wide variety of xenobiotics and endobiotics, such as drugs, carcinogens and steroid hormones. Metabolism of compounds by P450 3A3, 3A4 and 3A5 can be monitored and quantified using standard techniques to measure chemical metabolites. See, for example, Buters et al., *Drug Metab. Dispos.* 22: 688 (1994).

In particular, the antigen binding polypeptides of the invention can be used to determine the contribution of human cytochrome P450 3A3, 3A4 and 3A5 to the metabolism of a compound by quantifying the inhibition of P450-catalyzed chemical metabolism by an antigen binding polypeptide of the invention which inhibits the activity of human P450 3A3, 3A4 and 3A5. This method can be used with purified P450 enzymes to determine their substrate specificity and contribution to the metabolism of specific compounds. To determine the contribution of P450 3A3, 3A4 and 3A5 to compound metabolism by different tissues, the inhibition of compound metabolism by cell, tissue or microsomal preparations by the antigen binding polypeptides of the invention can be quantified. Thus, the samples to be analyzed—isolated P450s, cells, tissue or microsomes—are contacted with increasing amounts of an antigen binding polypeptide of the invention and the compound to be tested is added and its metabolism quantified. Another sample is not treated with the antigen binding polypeptide as a control. The inhibition of compound metabolism by an antigen binding polypeptide of the invention is directly proportional to the contribution of the P450 3A3, 3A4 and 3A5 to the metabolism of the compound tested.

In another preferred embodiment, the present invention relates to a method of determining the contribution of human P450 2E1 to the metabolism of compounds. Human P450 2E1 is responsible for the metabolism of a wide variety of small molecular weight xenobiotics, such as carcinogens. Metabolism of compounds by human P450 2E1 can be monitored and quantified using standard techniques to measure chemical metabolites. See, e.g., Guengerich et al., *Chem. Res. Toxicol.* 4: 168 (1991).

In particular, the antigen binding polypeptides of the invention can be used to determine the contribution of human cytochrome P450 2E1 to the metabolism of a compound by quantifying the inhibition of P450-catalyzed compound metabolism by an antigen binding polypeptide of the invention which inhibits the activity of human P450 2E1. This method can be used with a purified P450 enzyme to determine its substrate specificity and contribution to compound metabolism. To determine the contribution of P450 2E1 to compound metabolism in different tissues, the inhibition of compound metabolism by cell, tissue or microsomal preparations by the antigen binding polypeptide of the invention can be quantified. Thus, the samples to be analyzed are contacted with increasing amounts of an antigen binding polypeptide of the invention and the compound to be tested is added and its metabolism quantified. Another sample is not treated with the antigen binding polypeptide as a control. The inhibition of compound metabolism by an antigen binding polypeptide of the invention is directly proportional to the contribution of P450 2E1 to the metabolism of the compound tested.

The methods of determining the contribution of P450 to the metabolism of compounds of the present invention have a number of applications. These methods can be used to identify potential drug/drug interaction problems. If two different drugs are metabolized by the same P450 enzyme, the two drugs may compete with each other, leading to possible toxicity and/or reduced drug effectiveness. These quantification methods of the present invention can also be used to design drugs that utilize particular P450 enzymes so as to minimize drug/drug interactions and to maximize drug effectiveness.

It is known that different people have different P450 profiles. This phenomenon is commonly known as polymorphism for a particular trait. These differences lead to varying susceptibility to xenobiotics, including drugs. Knowledge of an individual's P450 profile can be used to design drug treatment plans that will have maximum effectiveness. Screening individuals for the presence and quantity of certain cytochrome P450s can be accomplished by using techniques such as Western blotting, which are well known in the art. In particular, an antigen binding polypeptide of the invention with the binding specificity of monoclonal antibody 2-106-12 can be used to screen for the presence and amount of human P450 2E1 in an individual. In particular, an antigen binding polypeptide with the binding specificity of monoclonal antibody 275-1-2 can be used to screen for the presence and amount of P450 3A3 and 3A4 in an individual. Any and all tissues and organs believed relevant to P450 metabolism can be examined, e.g., tissues of known carcinogen susceptibility.

Without further elaboration, it is believed that one skilled in the art can, using the preceding description, utilize the present invention to its fullest extent. The following examples are merely illustrative and not limitative of the remainder of the disclosure in any way whatsoever.

EXAMPLE 1

Preparation of Human P450 3A4 As Immunogen

Human cDNA for P450 3A4 was constructed into a baculovirus vector. SF9 insect cells were infected with the virus which expressed the P-450 3A4. See Buters et al., *Drug Metab. Dispos.* 22: 688 (1994). Purification of the P450 3A4 was accomplished by a series of extraction and column chromatography procedures which are fully described in Buters, supra.

EXAMPLE 2

Preparation of Vaccinia Virus-Expressed P450 cDNAs coding for different isozymes were constructed into vaccinia virus vectors. See Aoyama et al., *Proc. Nat'l Acad. Sci. USA* 87: 4790 (1990), and Battula et al., *Proc Nat'l Acad. Sci. USA* 84: 4073 (1987). The enzymes were expressed by infecting tk- or Hep G2 cells for 24–48 hours. The cell lysates were used as the source of P450 and the P450 content determined by spectral analysis. Cell lysates from infected tk- cells were used in ELISA and Western blotting, and cell lysates from Hep G2 cells were used for metabolic studies.

EXAMPLE 3

Immunization of Mice and Production of Hybridomas

Two female Balb/c mice were immunized by intraperitoneal injection weekly for three weeks with 10 μg of purified baculovirus expressed human 3A4 protein emulsified in 0.2 ml complete Freund's adjuvant for the first week, then with incomplete Freund's adjuvant thereafter. Three days after the third injection, one mouse was sacrificed and the spleen removed. The fusion of myeloma cells with primed, dissociated spleen cells was carried out essentially as described in Park et al., *Biochem. Pharmacol.* 35: 2859 (1986). Cells were diluted with HAT medium and dispensed into tissue culture plates.

EXAMPLE 4

Monoclonal Antibody Production, Screening, and Cross-Reactivity

ELISA analysis was made of 24 hybridoma clones that were selected from more than 700 clones and examined for their binding to baculovirus expressed P450 3A4. Due to the low yield of highly purified expressed protein, partially purified baculovirus expressed 3A4 was used for purposes of screening hybrids, and lysate from cells infected with wild type baculovirus was also used which went through the same partial purification scheme to check for specificity of the antibodies. As the hybrids began to grow, the spent media from each individual well with hybrid growth was screened for the presence of antibody to 3A4 as described above. Each individual well on the 96 well plates which had cell growth was assigned a number. Each positive well was re-screened and then cloned using complete media with 10% HCF. Hybrids of interest were cloned at least three times. Cloned hybrids producing monoclonal antibody were grown in flasks containing serum-free media (UltraDOMA-Biowhittaker) at a concentration of $5 \times 10^5$/ml for 3–5 days. Cells were removed by centrifugation and the resulting supernatant was concentrated with a Filtron Macrosep concentrator (mol. wt. cutoff 30,000). Concentrated monoclonal antibodies were dialyzed in PBS (pH 7.2). Ascites fluid was prepared as previously described in Park et al. *Biochem. Pharmacol.* 2859 (1986).

Of the 24 hybridomas tested, 15 yielded antibodies that were positive for specific binding to P450 3A4 by the ELISA test, six were high-to-moderate positive, and nine were moderately or negligibly positive. A positive sample is defined as one giving an ELISA value three times greater than the ELISA background value using as antigen proteins expressed from baculovirus containing no P450 cDNA. Of the 24 hybridomas, 13 were subcloned and one of the hybridoma clones, monoclonal antibody 275-1-2, yielded antibodies that gave an especially strong Western Blot. Seven of the hybridomas produced monoclonal antibody which were tested for inhibition of P450 3A4 catalyzed testosterone metabolism. Of all the hybridoma clones tested, monoclonal antibody 3-29-9 strongly inhibited, by 85%, human P450 3A4-catalyzed testosterone oxidation.

Western Blot analysis using monoclonal antibody 3-29-9 and monoclonal antibody 275-1-2 was performed. Antibody binding to baculovirus-expressed human P450 3A4, human P450 2E1, wild type control, vaccinia expressed human P450 3A3, 3A4, and 3A5, human liver microsomes, dexamethasone-induced rat liver microsomes and vaccinia-expressed rat 3A1 was measured. Proteins were electrophoretically separated on SDS-polyacrylamide gels (10%), transferred to nitrocellulose, then incubated with monoclonal antibody in culture or ascites fluid. Western blotting was performed according to the method in Ko et al., *Cancer Res.* 42: 3101–3109 (1987). Antibody binding was detected using alkaline phosphate conjugated goat anti-mouse antibodies. ELISA results are expressed as optical density (O.D.) values. The monoclonal antibody 275-1-2 shows strong Western Blot activity towards baculovirus-expressed human 3A4 and vaccinia expressed human 3A3 and 3A4, but did not recognize human 3A5. Thus monoclonal antibody 275-1-2 detects a common epitope in human 3A3 and 3A4 which is not present in 3A5 and thus monoclonal antibody 275-1-2 can distinguish between the closely related human 3A3, 3A4 and 3A5. The monoclonal antibody 275-1-2 also detected P450 3A3 and 3A4 in three different samples of human liver with one of the livers giving a second weaker band. The monoclonal antibody 275-1-2 detected two bands in the liver of dexamethasone treated rats. These are likely P450 3A1 and 3A2 of rat. The inhibitory monoclonal antibody 3-29-9 did not yield a Western Blot with any of the above samples. Vaccinia or baculovirus wild type proteins and human P450 2E1 were not recognized in Western Blotting with monoclonal antibody 275-1-2 or monoclonal antibody 3-29-9.

Table 3 shows the cross reactivity of monoclonal antibody 3-29-9 and monoclonal antibody 275-1-2 with a variety of vaccinia expressed and baculovirus-expressed human P450s as measured by the ELISA assay. Monoclonal antibodies used were from culture fluid or serum-free media (10 μg/ml). The O.D. values are the average from two experiments (vaccinia virus=vv; baculovirus=bv; P450=2–5 pmol/well).

TABLE 3

CROSS-REACTIVITY OF MAb 3-29-9 and MAb 275-1-2 to HUMAN 3A3/4 WITH RECOMBINANTLY-EXPRESSED HUMAN P-450

| P450 | O.D. MAb 3-29-9 | O.D. MAb 275-1 |
|---|---|---|
| bv3A4 | 0.89 | 1.34 |
| bv2E1 | 0.05 | 0.07 |
| bvWild | 0.09 | 0.13 |
| vv3A4 | 0.31 | 0.56 |
| vv3A3 | 0.41 | 0.71 |
| vv3A5 | 0.24 | 0.18 |
| vvWild | 0.09 | 0.15 |
| vv2C8 | 0.08 | 0.15 |
| vv2C9 | 0.09 | 0.16 |
| vv2B6 | 0.08 | 0.14 |
| vv2E1 | 0.09 | 0.17 |
| vv1A2 | 0.07 | 0.16 |

Both monoclonal antibody 3-29-9 and 275-1-2 made against baculovirus-expressed human 3A4 recognized baculovirus expressed human 3A4 but did not recognize baculo expressed human 2E1. Monoclonal antibody 3-29-9 also showed cross reactivity with vaccinia virus expressed human 3A4, 3A3, and to a lesser extent human 3A5. Monoclonal antibody 275-1-2 showed cross reactivity with human 3A3, 3A4 and only negligibly with human 3A5, which gave slightly greater cross reactivity than the wild type. Both monoclonal antibody 3-29-9 and monoclonal antibody 275-1-2 showed no cross reactivity with a variety of vaccinia expressed human P450s other than 3A3, 3A4, and 3A5. These included human 2C8, 2C9, 2B6, 2E1, and 1A2. This lack of cross reactivity of monoclonal antibody 3-29-9 and monoclonal antibody 275-1-2 with other major human P450s indicate that these new monoclonal antibody are of high specificity.

Table 4 shows that the monoclonal antibody 3-29-9 and monoclonal antibody 275-1-2 do not cross react with vaccinia expressed rat 3A1, rat 2A1, rat 4A1, rat 4A3, rat 2B1, mouse 1A1, and mouse 1A2. Monoclonal antibodies were from serum-free medium (10 μg/ml) (bv=baculovirus; vv=vaccinia virus; P450=2.5 mol/well). The ELISA O.D. values are the average of two experiments. There is slight cross reactivity of monoclonal antibody 275-1-2 with dexamethasone-induced rat liver microsomes.

TABLE 4

CROSS-REACTIVITY OF MAbs 3-29-9 AND 275-1-2 AGAINST RAT AND MOUSE EXPRESSED P450S BY ELISA

| P450 | O.D. MAb 3-29-9 | O.D. MAb 275-1-2 |
|---|---|---|
| bv h2E1 | 0.03 | 0.07 |
| bv h3A4 | 0.41 | 0.62 |
| bv Wild | 0.05 | 0.05 |
| DEX MICS | 0.02 | 0.24 |
| vv r3A1 | 0.03 | 0.11 |
| vv r2A1 | 0.03 | 0.15 |
| vv r4A1 | 0.02 | 0.05 |
| vv r4A3 | 0.02 | 0.07 |
| vv Wild | 0.02 | 0.06 |
| Vv m1A1 | 0.03 | 0.16 |
| vv m1A2 | 0.02 | 0.05 |
| vv r2B1 | 0.02 | 0.06 |

EXAMPLE 5

Inhibitory Effect of the Monoclonal Antibody 3-29-9 On P450 3A3, 3A4 And 3A5

The monoclonal antibody 3-29-9, in a concentration ranging from 10 to 1000 μg, was pre-incubated with 10–50 pmol of P450 3A4, 3A3, 3A5, or human microsomes or dexamethasone-induced rat liver microsomes in 100 μl of 50 mM potassium phosphate buffer (pH 7.4) at 37° C. for five minutes. The mixture was then diluted with buffer to 1 ml final volume. Test compounds dissolved in 10 μl of methanol (250 μM of testosterone, 80 μM of diazepam, 100 μM of taxol, 10 μM of cyclosporin, 100 μM of phenanthrene or 150 μM of nitroanisole, as final concentration) were added and the reaction was initiated by addition of NADPH (1 mM) at 37° C. Anti-lysozyme monoclonal antibody HyHel or monoclonal antibody 1-68-11 against rat 2C11 in amount equivalent to that of the 3A4 monoclonal antibody were used as controls for nonspecific binding. Reactions were followed for 20 to 30 minutes, and were terminated with 5 volumes of dichloromethane (DCM), except for the metabolism of cyclosporin. 6β-OH-progesterone, OQZ and deuterated nitrophenol were used respectively as internal standards in metabolism of testosterone, diazepam and nitroanisole, and B[a]P 9,10-diol was used as an internal standard in metabolism of taxol, cyclosporin and phenanthrene for quantification of the products formed. See Hanioka et al., *Protein Eng'rg* 3: 571 (1990); Yang, *J. Liquid Chromatogr.* 16: 2605 (1993); Harris et al., *Cancer Res.* 54: 4026 (1994); Prueksaritanonte et al., *Biochem. Pharmacol.* 43: 1977 (1992); and Shou et al., *Cancer Lett.* 83: 305 (1994).

Extracts of products were dissolved in methanol and analyzed immediately by reversed phase HPLC. Metabolites formed were identified by comparing their retention times with authentic standards. Metabolically formed nitrophenol ($D_0$) from nitroanisole and internal standard ($D_4$-nitrophenol) were further derivatized and analyzed by GC-MS as follows: The sample was concentrated to 100 μl and derivatized with t-butyldimethysilytrifluoroacetamide containing 1% t-butyldimethysislyl chloride. The derivatized phenols were quantified by GC-MS using an Alltech AT-1 column (30 m×0.25 mm; 1.0 μm film thickness) and a Hewlett Packard 5971 Mass Selective Detector. Samples were injected at 50° C., ramped at 30° C./min to 150° C. followed by 10° C./min to 280° C. The derivatized nitrophenols eluted at 16.3 min and were quantitated by integrating the peak areas at masses 253 and 257. For achieving higher recoveries of cyclosporin and its metabolites, a modified procedure was utilized. Three milliliters of a mixture of 20% acetonitrile, 30% methanol and 5% zinc sulfate in water were added to precipitate the proteins. Samples were centrifuged at 3000 rpm in a Sorvall RT600 centrifuge (Du Pont Co., Wilmington, Del.) after the addition of B[a]P 9,10-diol (internal standard) and the supernatant was loaded onto Sep-Pak cartridge $C_{18}$ (Millipore Corp., Milford, Mass.) washed with 2 ml of water, and eluted with 4 ml of methanol. The eluent was evaporated to dryness under a stream of nitrogen and the residue was dissolved in 50% methanol in water for further HPLC analysis.

The HPLC was performed on a Hewlett-Packard Mode HP1050 liquid chromatograph equipped with an HP Model 1050 autosampler, a ternary solvent delivery system and a multiple-wavelength detector, all controlled by Hewlett Packard HPLC$^{2D}$ ChemStation software installed a Compaq Prolinea 4/66 personal computer.

Diazepam (DZ) and its metabolites (temazepam (TMZ) and desmethyldiazepam (NDZ)) were separated on a Zorbax SB-C18 column (4.6 mm×15 cm, MAC-MOD Analytical Inc., Chadds Ford, Pa.) and eluted isocratically with acetonitrile/methanol/water (10:40:50, v/v/v) at a flow rate of 1 ml/min and a detection of 232 nm. Cyclosporin and metabolites were injected onto an Ultrasphere™-octyl column (5 μm, 25 cm×4.6 mm, ALTEX). The elution of metabolites was used with a 65:30:5 mixture of diluted phosphoric acid (pH=3):acetonitrile:tetrahydrofuran for 5 min, and a 23 min linear gradient to 60:35:5 and 12 min to 38:57:5 at a flow rate of 1 ml/min and a detection of 230 nm. The metabolites of taxol, testosterone, or phenanthrene were separated and identified as previously described. See Harris et al., *Cancer Res.* 54: 4026 (1994); Hanioka et al. (1990), supra; and Shou et al., *Cancer Lett.* 83: 305 (1994).

Different molecular weight substrates were used to examine the possibility that the monoclonal antibody 3-29-9 inhibition of P450 3A3 and 3A4 was limited to substrates of unique molecular size which could reflect a unique binding of the substrate or the monoclonal antibody with the P450 3A4 epitope. However, monoclonal antibody 3-29-9 inhibited the metabolism of substrates with very diverse molecular sizes and characteristics.

As shown in FIG. 1, monoclonal antibody 3-29-9 inhibited P450 3A3 catalyzed p-nitroanisole metabolism by 45% and by P450 3A4 by 60%. Metabolism of p-nitroanisole by P450 3A5 was inhibited by only 26%. Specific activities (nmol/min, nmol of P450 in the formation of nitrophenol) for 3A4, 3A3, 3A5, HLM and 2E1 without monoclonal antibody 3-29-9 were 0.20, 0.21, 0.14, 4.93, and 7.80, respectively. The compound p-nitroanisole is not considered a good substrate for 3A3 and 3A4; accordingly, it may be uniquely insensitive to inhibition. The metabolism of p-nitroanisole by rat microsomes induced for P450 3A1/3A2 activity by dexamethasone was not inhibited by the monoclonal antibody 3-29-9. Thus, monoclonal antibody does not cross react by inhibition of rat P450 3A1/2. Human P450 2E1, used as a control, is an enzyme highly active in the metabolism of p-nitroanisole and was not inhibited by monoclonal antibody 3-29-9. Human liver microsomes display metabolic activity towards p-nitroanisole. However, monoclonal antibody 3-29-9 did not inhibit p-nitroanisole metabolism in human liver. These results suggest that p-nitroanisole metabolism in human liver is a function of P450s other than P450 3A3 and 3A4 and 3A5.

Figure 2:
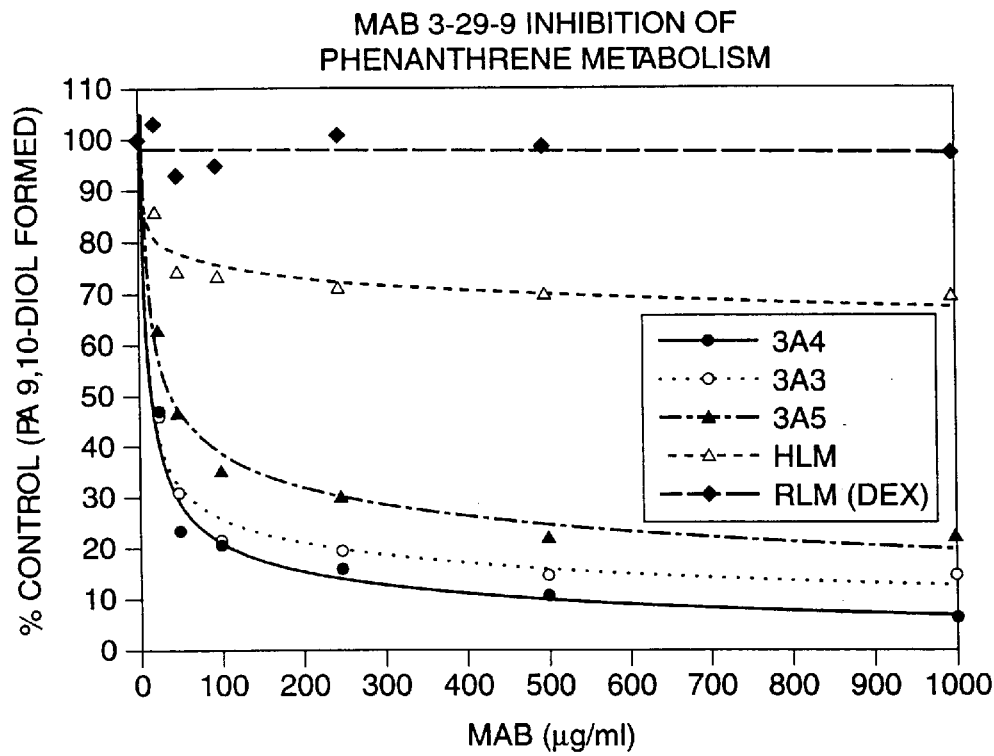
FIG. 2 shows monoclonal antibody 3-29-9 inhibition of phenanthrene metabolism. P450 and monoclonal antibody 3-29-9 were preincubated in KPi buffer for 5 minutes. Phenanthrene, NADPH and KPi were added and incubated for 25 minutes, and the reaction was terminated with DCM. B[a]P 9,10-diol was added as an internal standard. Extracts were dried down and analyzed by reversed-phase HPLC. Percentage of control was calculated as described with respect to FIG. 1.

The metabolism of phenanthrene by P450 3A3, 3A4 and 3A5 and its inhibition by the monoclonal antibody 3-29-9 was examined. Phenanthrene is known to be metabolized by P450 3A3, 3A4 and 3A5 and by microsomes from dexamethasone-treated rats and by human liver microsomes. As shown in FIG. 2, monoclonal antibody 3-29-9 inhibited phenanthrene metabolism catalyzed by P450 3A4 by 97%. P450 3A3 catalyzed metabolism was inhibited by 86% and P450 3A5 catalyzed metabolism was inhibited by about 78%. Human liver microsomes were inhibited by 30%, which indicates that human P450 3A3, 3A4 and 3A5 contribute not less than 30% to the metabolism of phenanthrene in human liver. In rat liver microsomes from dexamethasone treated rats, no inhibition by monoclonal antibody 3-29-9 was observed. This is consistent with the fact that monoclonal antibody 3-29-9 does not cross react with dexamethasone induced P450 3A1/2 in rat liver. The determination of 30% inhibition in human liver by monoclonal antibody 3-29-9 demonstrates the value of a monoclonal antibody for determining the quantitative role of an individual P450 in a tissue containing a variety of P450s.

Figure 3A:
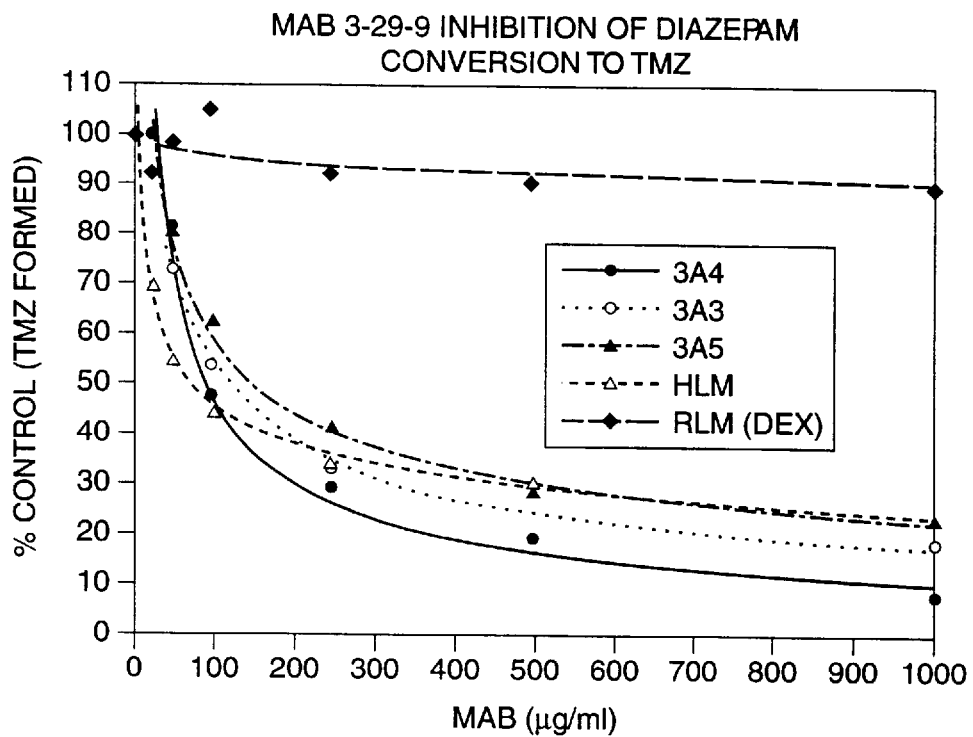
FIGS. 3A and 3B show monoclonal antibody 3-29-9 inhibition of diazepam conversion to temazepam (TMZ) and N-desmethyldiazepam (NDZ). P450 and monoclonal antibodies were preincubated for 5 min and diazepam and NADPH were added. Incubations were carried out for 20 min and terminated with DCM; 2-oxoquanzepam (OQZ) was added as an internal standard. Extracts were dried and dissolved in 50% methanol for HPLC analysis. Percentage of control was calculated as described in the description of FIG. 1.
Figure 3B:
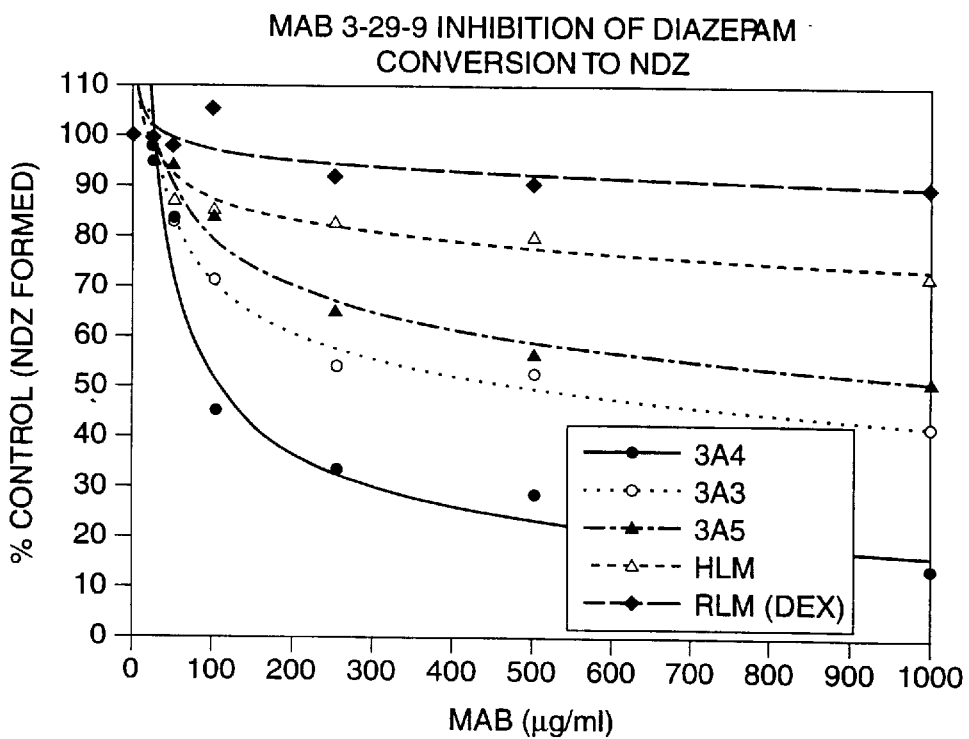

Diazepam is one of the most common clinically used drugs in the world. Diazepam is converted by P450 3A3 and 3A4 to the metabolite TMZ by hydroxylation of the ring and to the metabolite NDZ by demethylation. As shown in FIGS. 3A and B, monoclonal antibody 3-29-9 is a strong inhibitor of both human P450 3A3 and 3A4 catalyzed diazepam metabolism. The formation of the two major diazepam metabolites TMZ and NDZ by P450 3A4 was inhibited by monoclonal antibody 3-29-9 by 92% and 87%, respectively, and metabolite formation by P450 3A3 was inhibited by approximately 80% for TMZ and 48% for NDZ. Diazepam metabolism catalyzed by 3A5 was inhibited by monoclonal antibody 3-29-9 by 73% for TMZ and by 52% for NDZ. Specific activities for the formation of TMZ (nmol/min, nmol of P450) for 3A3, 3A4, 3A5, HLM and dexamethosone induced RLM, without monoclonal antibody 3-29-9, were 20.7, 15.4, 19.6, 9.2 and 50, and in the formation of NDZ were 4.1, 2.7, 2.1, 2.0 and 8.5, respectively. Examination of the metabolism of diazepam by human liver microsomes shows that TMZ metabolite formation is largely due to P450 3A3, 3A4 and 3A5 since monoclonal antibody 3-29-9 added to human liver microsomes diazepam to TMZ conversion by 75% and NDZ by 27%. The difference in inhibition of TMZ and NDZ formation in human liver by monoclonal antibody 3-29-9 indicates that there are at least two types of P450 enzymes in liver responsible for diazepam metabolism. One type is P450 3A3, 3A4 and 3A5 and the other has not been identified.

Figure 4:
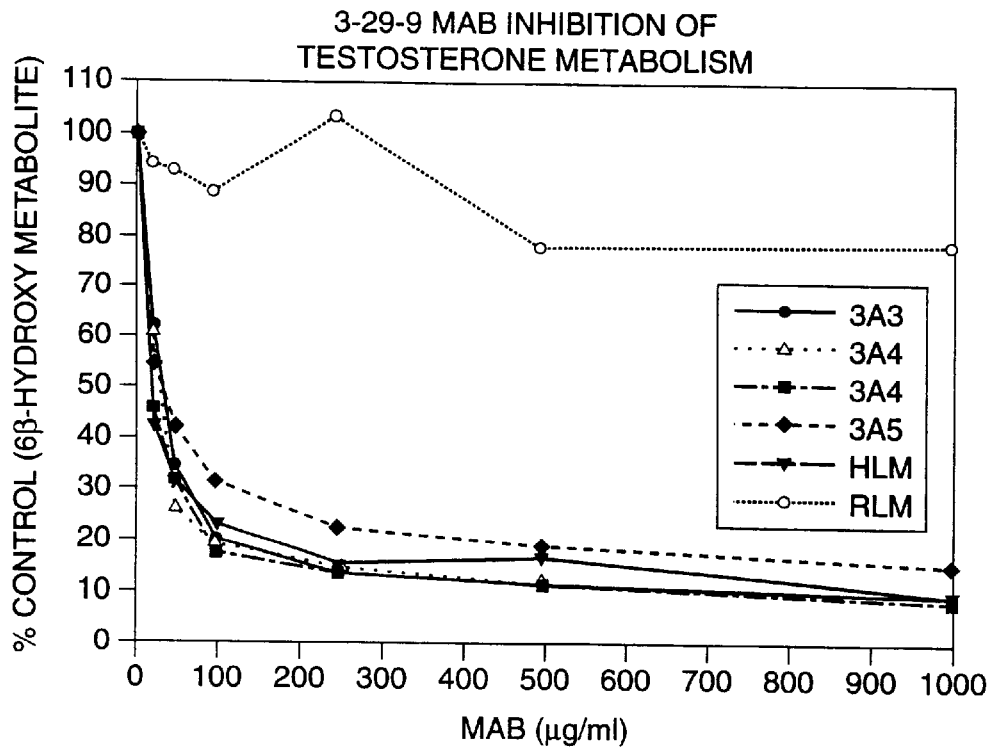
FIG. 4 shows inhibition by Mab 3-29-9 of testosterone conversion to the 6β-OH metabolite. P450s and monoclonal antibodies were preincubated for 20 minutes. Testosterone, NADPH and KPi were added and incubated for 20 minutes. Metabolites were extracted with DCM and analyzed by HPLC. Percentage of control was calculated as described with respect to FIG. 1.

Human Cytochrome P450 3A4 metabolizes a large diverse number of steroids, a prototype of which is testosterone. As shown in FIG. 4, monoclonal antibody 3-29-9 was a potent inhibitor of human P450 3A3, 3A4, and 3A5 catalyzed conversion of testosterone to 6β-hydroxy testosterone. Similar inhibition was observed for the formation of 15β-OH testosterone (data not shown). The addition of monoclonal antibody 3-29-9 to human liver microsomes inhibited 6β OH formation more than 90%, indicating that P450 3A3, 3A4 and 3A5 are essentially the sole P450s responsible for testosterone metabolism by human liver. Specific activities for 3A3, 3A4, 3A5, HLM and MLM in the formation of 6β-OH testosterone, without monoclonal antibody, 3-29-9 were 25, 25, 10, 2.0 and 65, respectively.

Figure 5:
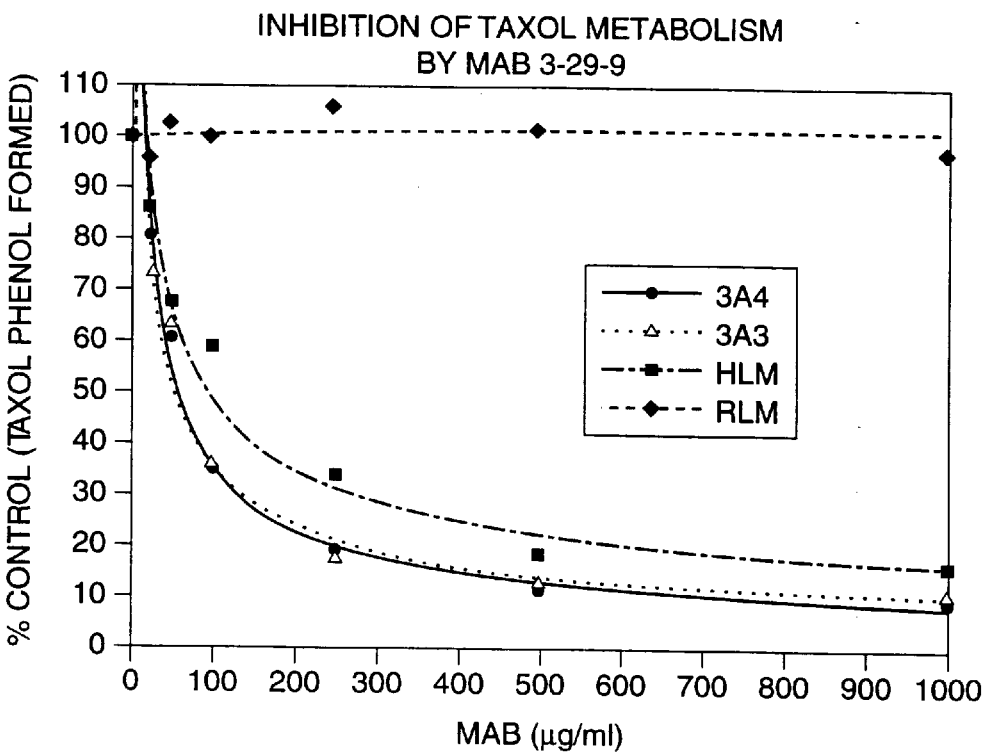
FIG. 5 shows inhibition of taxol metabolism by monoclonal antibody 3-29-9. P450 was preincubated with monoclonal antibody 3-29-9 for 5 min at 37° C. Taxol, NADPH and KPi were added and incubated for 30 minutes. Incubation was terminated with DCM, and B[a]P 9,10-diol, an internal standard, was added. The extracts were analyzed by HPLC. Percentage of control was calculated as described with respect to FIG. 1.

Taxol is known to be metabolized by the human P450 3A4 system and is a very important compound currently used in the therapy of certain kinds of cancer. Taxol phenol has been characterized as a major product of taxol metabolism by human P450 3A4. As shown in FIG. 5, Taxol conversion to phenol by human P450 3A3 and 3A4 was inhibited by the monoclonal antibody 3-29-9 by about 90%. Human liver microsome metabolism of taxol was inhibited by monoclonal antibody 3-29-9 by 84% which indicates clearly the very dominant and important roles of P450 3A3 and 3A4 for taxol metabolism in human liver. Thus, 84% of taxol metabolism in human liver is due to P450 3A3 and 3A4. The liver microsomes obtained from pregnenolone-alpha-carbonitrile-treated rats showed total resistance to inhibition by monoclonal antibody 3-29-9 and retained 97% of their usual activity in the presence of the monoclonal antibody.

Figure 6:
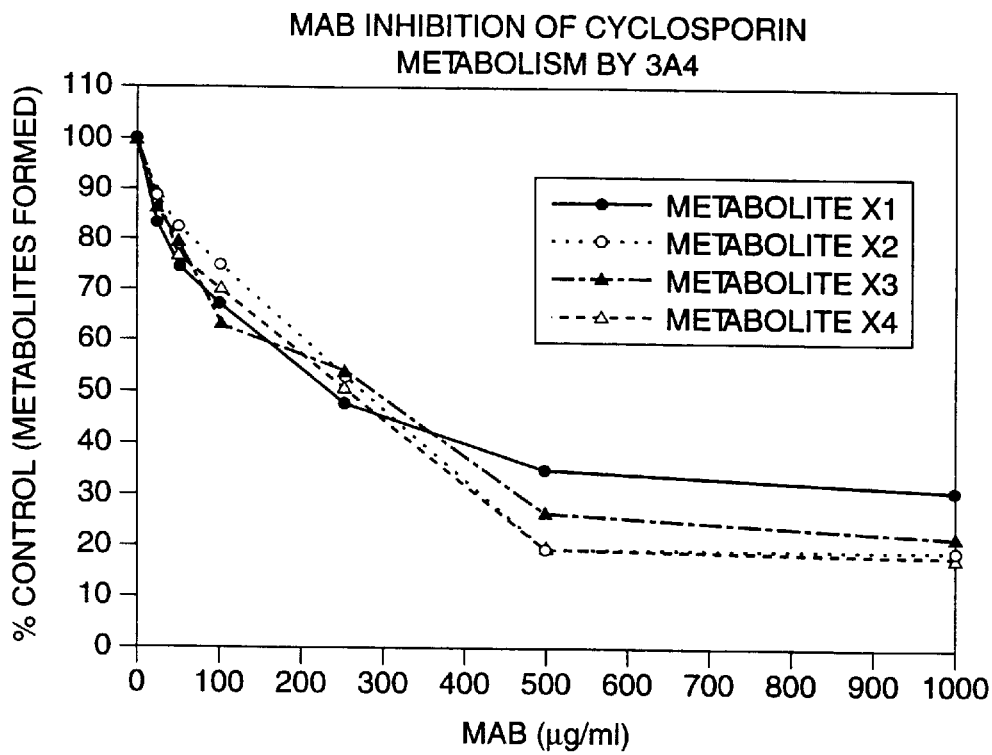
FIG. 6 shows monoclonal antibody 3-29-9 inhibition of cyclosporin metabolism. P450 was preincubated in KPi with Mab 3-29-9 for 5 min at 37° C. Cyclosporin and NADPH were added, and incubations were carried out for 20 minutes. Extracts were analyzed by HPLC. Percentage of control was calculated as described above.

Cyclosporin is a very important drug for suppressing the immune response and is crucial for organ transplants. It has a relatively high molecular weight. As shown in FIG. 6, the HPLC analysis of cyclosporin metabolism shows that the formation of all four metabolites of cyclosporin by P450 3A4 was inhibited to approximately the same extent by monoclonal antibody 3-29-9. This inhibition ranged from 70%–85% for the formation of each of the four metabolites. Thus, the metabolism of a very large molecule such as cyclosporin is catalyzed by P450 3A4 and is inhibited by monoclonal antibody 3-29-9.

EXAMPLE 6

Preparation of Baculovirus Expressed P450 2E1

*Spondoptera frugipedra* (Sf9) cells were infected with a recombinant baculo virus containing human P450 2E1 cDNA. See Gonzalez, et al. Meth. Enzymol. 206:93–99 (1991). The expressed human 2E1 was purified from cell membrane fractions using hydrophobic interaction and hydroxylapatite chromatography as described in Laethem et al., *J. Biol. Chem.* 268: 12912 (1993).

EXAMPLE 7

Preparation of Vaccinia Virus-Expressed P450S for use in 2E1 Experiments cDNAs coding for different cytochrome P450 isozymes were constructed into vaccinia vector as described in Gu et al., *Pharmacogenetics* 2:73 (1992). The following enzymes were expressed in TK embryoblasts or Hep G2 cells infected with recombinant vaccinia viruses: human 1A2, 2B6, 2C8, 2C9, 2E1, 3A3, 3A4, 3A5; mouse 1A1 and 1A2 and rat 2B1/2. The cells were harvested 24–48 hours after infection. The membrane fractions of Hep G2 cells were used as a source of individual P450s for metabolic studies after measurement of enzyme content by spectral analysis according to the method of Kharasch et al., *Clinic. Pharmacol. Therapeut.* 55: 434 (1994). Cell lysates from infected TK embryoblasts or Hep G2 cells were used in ELISA and immunoblotting.

EXAMPLE 8

Production and Purification of Monoclonal Antibodies to 2E1

Two female Balb/c mice were inoculated intraperitoneally with the purified baculovirus-expressed recombinant human 2E1 protein. Following a series of booster inoculations, spleenocytes were taken one week, two weeks and 6 months after initial inoculation. Fusion of the spleen cells and mouse non-secreting myeloma P3/NSI/1-Ag4-1 (NS-1) was performed as described previously in Mraz et al., *Chem. Res. Toxicol.* 6:197 (1993), with some modifications: the fused cells were plated in microtiter wells at a density of $1.5 \times 10^4$ cells per well, and HAT medium was supplemented with 10% Hybridoma Cloning Factor from IGEN, Inc. Microtiter wells were examined daily for growing hybridomas starting with the 7th day after fusion until the time when no new hybridomas were observed. Spent medium of hybridomas approaching confluence was tested in ELISA with baculo-expressed h2E1 as antigen. See Goldfarb, et al. *Biochem. Pharmacol.* 46:787–790, 1993. Samples showing a positive response were immediately tested for cross-reactivity with wild type, baculo-expressed antigen. Those showing at least a four-fold stronger signal with baculo-expressed human 2E1 as compared to wild type antigen were considered specific for P450 h2E1. Hybridomas producing specific immunoglobulins (Ig) were subcloned by limiting dilution. Monoclonal antibodies recovered from cloned hybrids were further tested for immunoprecipitation and for their ability to inhibit h2E1-catalyzed metabolism of phenanthrene and Isotyping of monoclonal antibodies was carried out using alkaline phosphatase conjugated affinity purified anti-mouse IgG1, IgG2a, IgG2b and IgM from Zymed Laboratories, Inc. (San Francisco, Calif.). Large-scale production of monoclonal antibodies was achieved by growing cloned hybridomas in culture. Immunoglobulin (Ig) proteins from hybridoma culture supernatants were precipitated with 50% saturated ammonium sulfate, then dialyzed in PBS, aliquoted and stored at −20° C.

Additional amounts of monoclonal antibody 1-73-18 were prepared in ascites fluid. Monoclonal antibody producing hybridomas were subcloned three times, expanded and injected into pristane-primed BALB/c mice for production of ascites fluid. In two weeks, the ascites fluid was taken, aliquoted and stored at −20° C. The concentration of 1-73-18 in ascites fluid was 2.0 to 0.5 mg per ml.

EXAMPLE 9

Cross-Immunoreactivity of Monoclonal Antibodies

All seventeen monoclonal antibodies were tested in ELISA for their binding activity with recombinant antigens of different P450 isoforms. The concentration of immunoglobulins used in each series of the experiment was: 10.0, 1.0 and 0.1 µg per ml. No binding occurred between any of the 17 monoclonal antibodies with baculo-expressed human 3A4 or with vaccinia-expressed human 1A2, 2C8, 2C9, 3A3, 3A4, and 3A5. As shown in Table 5, monoclonal antibodies 1-73-18 and 1-42-4 reacted with the homologous h2E1 antigen but did not bind any of the heterologous expressed antigens. ELISA results are expressed as O.D. values.

TABLE 5

ELISA analysis of cross-reactivity of Mabs 1-73-18 and 1-42-4 to baculo-expressed h2E1 with heterologous baculo and vaccinia-expressed human P450s.

| P450s | Mab 1-73-18[a] | Mab 1-42-4 |
|---|---|---|
| bv2E1 | 1.361 | 1.890 |
| bv3A4 | 0.033 | 0.024 |
| bvWild | 0.046 | 0.041 |
| vv1A2 | 0.119 | 0.139 |
| vv2C8 | 0.112 | 0.138 |
| vv2C9 | 0.130 | 0.152 |
| vv2E1 | 0.407 | 0.789 |
| vv3A3 | 0.147 | 0.172 |
| vv3A4 | 0.134 | 0.150 |
| vv3A5 | 0.124 | 0.135 |
| vvWild | 0.147 | 0.126 |

[a]Assay: ELISA using 5 pmol per well of expressed P450s from vaccinia (vv) and 1 pmol per well from baculo virus (bv). Mab concentration is 1 µg/ml.

A summary of cross reactivity between each monoclonal antibody and baculo-expressed and vaccinia-expressed h2E1 antigens in ELISA and immunoblots (IB) is presented in Table 6.

TABLE 6

ELISA and IB analysis of binding of Mabs against baculo-expressed h2E1 with vaccinia-expressed h2E1 and rat 2E1 from microsomes of acetone-induced rat liver.

| Mabs | Ig class | ELISA[a] baculo-h2E1 1 pmol | vaccinia-h2E1 1 pmol | RLM[c] 5 pmol | Immunoblot[b] baculo-h2E1 1 pmol | vaccinia-h2E1 1 pmol | RLM 3 pmol | Inhibition[d] |
|---|---|---|---|---|---|---|---|---|
| 1-10-3 | G | 1.89 | 0.62 | 0.17 | (+) | (+) | n.t.[f] | − |
| 1-18-27 | G | 1.66 | 0.31 | 0.04 | + | + | n.t. | − |
| 1-42-4 | G | 1.95 | 0.74 | 0.52 | − | — | n.t. | − |
| 1-48-1 | G | 1.44 | 0.20 | 0.14 | +++ | +++ | +++ | − |
| 1-83-1 | G | 1.61 | 0.20 | 0.12 | +++ | +++ | +++ | − |
| 1-93-5 | G | 1.94 | 0.74 | 0.76 | + | n.d.[e] | + | − |
| 1-393-1 | G | 1.41 | 0.07 | 0.05 | +++ | +++ | +++ | − |
| 1-36-1 | M | 0.95 | 0.27 | 0.61 | ++ | + | ++ | − |
| 1-53-1 | M | 1.22 | 0.27 | 0.41 | + | + | + | − |
| 1-67-3 | M | 0.85 | 0.15 | 0.23 | +++ | +++ | +++ | − |
| 1-72-6 | M | 0.81 | 0.14 | 0.26 | ++ | ++ | ++ | − |
| 1-73-18 | M | 1.28 | 0.43 | 0.10 | − | − | − | + |
| 1-88-11 | M | 1.57 | 0.51 | 0.42 | (+) | (+) | (+) | − |
| 1-156-3 | M | 0.51 | 0.10 | 0.34 | +++ | +++ | − | − |
| 2-24-7 | G | 1.99 | 0.97 | 0.17 | ++ | + | − | − |
| 2-106-12 | G | 1.87 | 0.18 | 0.16 | ++ | ++ | ++ | − |
| 2-155-45 | G | 1.99 | 0.26 | 0.21 | +++ | +++ | +++ | − |

[a]Antigen-binding activity was determined at 405 nm.
[b]Qualitative estimates of antigen-binding activity.
[c]Aceton-induced rat liver microsomes.
[d]Metabolism of phenanthrene and p-nitroanisole was carried out respectively for screening inhibitory Mabs as listed above The results shown are for an immunoglobulin concentration of 10 µg/ml. Four monoclonal antibodies of IgG class (1-10-3, 1-42-4, 1-93-5, 2-24-7) and two of IgM class (1-73-18, 1-88-11) reacted with vaccinia-expressed h2E1. Five of the 17 tested monoclonal antibodies cross-reacted with liver microsomes from acetone treated rats (1-42-4, 1-93-5, 1-36-1, 1-53-1, 1-88-11). The remaining 11 tested monoclonal antibodies did not cross react with liver microsomes from acetone treated rats and liver microsomes from non-treated rats even at a concentration of 100 µg/ml immunoglobulin.

Qualitative estimation of antigen-binding activity of monoclonal antibodies in an immunoblot assay is also presented in Table 6. Thirteen monoclonal antibodies binding baculo virus-expressed human 2E1 were tested for their binding to acetone treated rat liver microsomes; qualitative estimation of their immunoprecipitation is shown in Table 6. Only two monoclonal antibodies, 2-24-7 (IgG) and 1-156-3 (IgM), did not recognize P450 2E1 in acetone treated rat liver microsomes. Binding activity of monoclonal antibodies to rat 2E1 was as strong as with baculo-expressed h2E1.

Immunoblotting was performed using monoclonal antibodies 2-106-12 according to the technique described in Ko, et al. *Cancer Res.*, 47:3101–3109, 1987. Briefly, proteins were electrophoretically separated on SDS-polyacrylamide gels, transferred to nitrocellulose and probed with monoclonal antibody in culture or ascites fluid. Monoclonal antibody 2-106-12 specifically bound to baculo-expressed human 2E1 and vaccinia-expressed human 2E1. There was no cross-reaction of 2-106-12 with vaccinia-expressed human 1A2, 2B6, 2C8, 2C9, 3A3, 3A4, 3A5, mouse 1A1 and 1A2, rat 2A1 and 2B1. Antibody 2-10-12 recognized a single band microsomes from acetone and dexamethasone treated and untreated rats. The microsomal fraction of two human livers showed strong 54 kDa bands when tested with monoclonal antibody 2-106-12.

EXAMPLE 10

Inhibition of 2E1-Catalyzed Metabolism

Monoclonal antibodies, at protein concentrations ranging from 10 to 500 µg, were preincubated with 10-50 pmol of vaccinia-expressed human 2E1 or human liver microsomes or acetone induced rat liver microsomes in 100 µl of 50 mM potassium phosphates buffer (pH 7.4) in a final volume of 1 ml at 37° C. for 5 minutes. The mixture was then diluted with potassium phosphate buffer to 0.97 ml. Substrate and NADPH (1 mM) were added in 1 ml final volume to initiate the reaction. The concentration of the substrate was 150 mM for p-nitroanisole, 200 mM for phenanthrene, and 500 mM for chlorzoxazone, toluene or 4-methylanisole. Four volumes of dichloromethane (DCM) were added to stop the reaction after 20 minutes. Monoclonal antibodies 1-68-11 (IgM class against rat 2C11) or Hy Hel (IgG against hen eggwhite lysozomes) at an amount of protein equivalent to the monoclonal antibody to human 2E1 were used as controls. Internal standards, B[a]P 9,10-diol for metabolism of phenanthrene or chlorzoxazone, deuterated nitrophenol for metabolism of nitroanisole, and benzyl alcohol (D7) for metabolism of toluene or 4-methylanisole, were added for metabolic quantification. Extracts of products were analyzed by either reversed phase high performance liquid chromatography (HPLC) or gas chromatography-mass spectroscopy (GC-MS) when necessary.

HPLC was performed on a Hewlett-Packard Mode HP1050 liquid chromatograph equipped with an HP model 1050 autosampler, a ternary solvent delivery system and a multiple-wavelength detector, controlled by Hewlett Packard HPLC$^{2D}$ ChemStation software installed in a Compaq Prolinea 4/66 personal computer. The separation of phenanthrene metabolites was analyzed is previously reported in Duescher et al., *Arch. Biochem. Biophy.* 342 (1994). Chlorzoxazone and its 6-hydroxy metabolite were separated on a 20/20 ODS column (4.6 mm i.d.×200 mm,TLC, Springfield, Va.), eluted with a gradient of 10% acetonitrile in water containing 0.5% $H_3PO_4$ (pH=3) to 80% acetonitrile at a flow rate of 1 ml per minute. Retention times of 6-hydroxy metabolite and chlorzoxazone were 9.0 and 13.2 min, respectively.

GC-MS analysis was performed on a Hewlett-Packard 5890 instrument with a 5971 mass selective detector and a HP Vectra QS/20 PC computer using HP-G1030A MS ChemStation (DOS series) software. A Heliflex (Deerfield, Ill.) AT-1 silica capillary column (30 m×0.25 mm×1 um film) was used. Metabolites of nitroanisole and toluene with MtBSTFA (metabolites of 4-methylanisole with BSA) were derivatized at 60° C. overnight to butyldimethylsilyl (trimethylsily) products. Samples were injected into a column via an autosampler and eluted with carrier gas of helium under 6 psi. Ionization was by electron impact (70 eV). The program was carried out at a gradient of 50° to 150° C. at 30°1 C./minute, and then from 150° to 280° C. at 10° C./minute.

Figure 7:
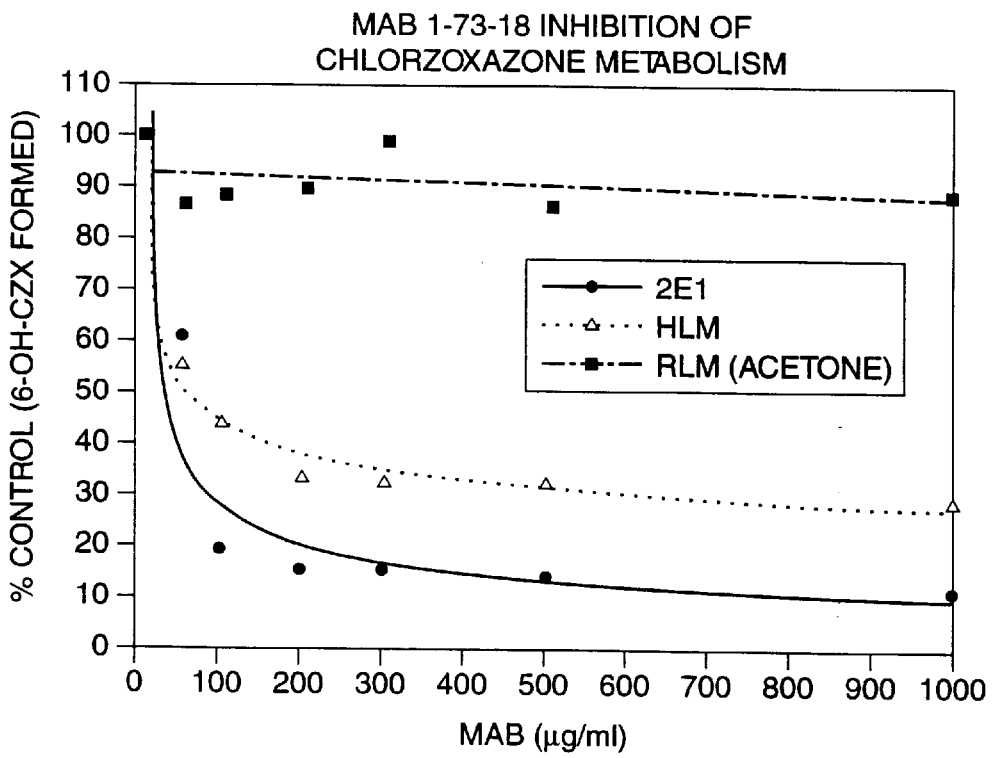
FIG. 7 shows monoclonal antibody 1-73-18 inhibition of chlorzoxazone metabolism. Monoclonal antibody 1-73-18 was preincubated with 2E1, HLM or acetone-induced RLM in KPi for 5 min at 37° C. Chlorzoxazone and NADPH were added and incubated for 20 minutes. Monoclonal antibody 1-68-11 (IgM for rat 2C11) was used as a control. The reaction was terminated with dichloromethane, and B[a]P 9,10-diol was added as an internal standard. Extracts were analyzed by reversed-phase HPLC. Percentage of control is expressed as [(metabolite formed/internal standard) with 1-73-18]/[(metabolite formed/internal standard) without 1-73-18].

Monoclonal antibody 1-73-18 specifically inhibited the enzyme activity of human P450 2E1. Chlorzoxazone, a centrally acting muscle relaxant, is oxidized only to 6-hydroxychlorzoxazone in human liver and human 2E1 is known to be the primary catalyst of chlorzoxazone 6-hydroxylation. See Camus et al., *Mol. Carcinog.* 7:268–275, 1993, and Yamazaki et al., *Carcinogenesis* 13:1789–1794, 1992. As shown in FIG. 7, monoclonal antibody 1-73-18 inhibited the human 2E1-catalyzed metabolism of chlorzoxazone by 89%. The addition of monoclonal antibody 1-73-18 to human liver microsomes resulted in the inhibition of chlorzoxazone metabolism by 71%. In contrast, no inhibition of chlorzoxazone metabolism by monoclonal antibody 1-73-18 was observed in liver microsomes from acetone-treated rats.

Figure 8:
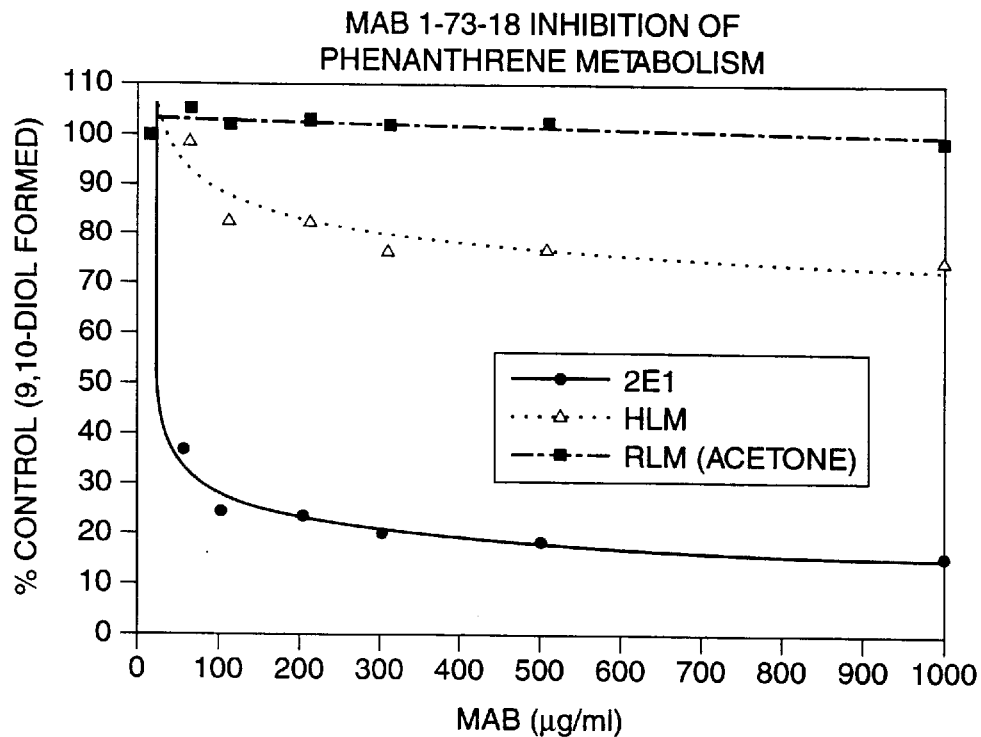
FIG. 8 shows monoclonal antibody 1-73-18 inhibition of phenanthrene metabolism. Monoclonal antibody 1-73-18 was preincubated with 2E1, HLM or acetone-induced RLM in Kpi for 5 min at 37° C. Phenanthrene and NADPH were added and incubated for 20 minutes. Monoclonal antibody 1-68-11 against rat 2C11 was used as a control. The reaction was terminated with dichloromethane, and B[a]P 9,10-diol was added as an internal standard. Extracts were analyzed by reversed-phase HPLC. Percentage of control was calculated as described in FIG. 7.

As shown in FIG. 8, monoclonal antibody 1-73-18 inhibited human 2E1-catalyzed metabolism of phenanthrene to the primary 9,10-diol by 84%. Phenanthrene metabolism by human liver microsomes was inhibited by 25%, suggesting that human 2E1 contributes 25% of the total enzymatic activity responsible for phenanthrene metabolism. The remaining 75% of the total phenanthrene metabolism is catalyzed by P450 isoforms other than h2E1. No inhibition of 2E1 by monoclonal antibody 1-73-18 was observed in acetone-induced liver microsomes.

The effect of monoclonal antibody 1-73-18 on human 2E1-catalyzed metabolism of benzene derivatives such as p-ntroanisole, toluene and 4-methylanisole was examined. These molecules are substrates for 2E1 with high turnover rates. See Yamazaki et al., *Carcinogenesis* 13: 979–985, 1992, and Lauriault et al., *Chem. Biol. Interact.* 81:271–289, 1992. The compound p-nitroanisole is demethylated by P450 to form nitrophenol. Deuterated nitrophenol (D4) was used as an internal standard for both identification and quantification of product by GC-MS as recently described in Duescher et al., *Anal. Biochem.* 311 (1993). The specific activity of human 2E1 for conversion of substrate to nitrophenol was approximately 11 nmol/minute.

Figure 9:
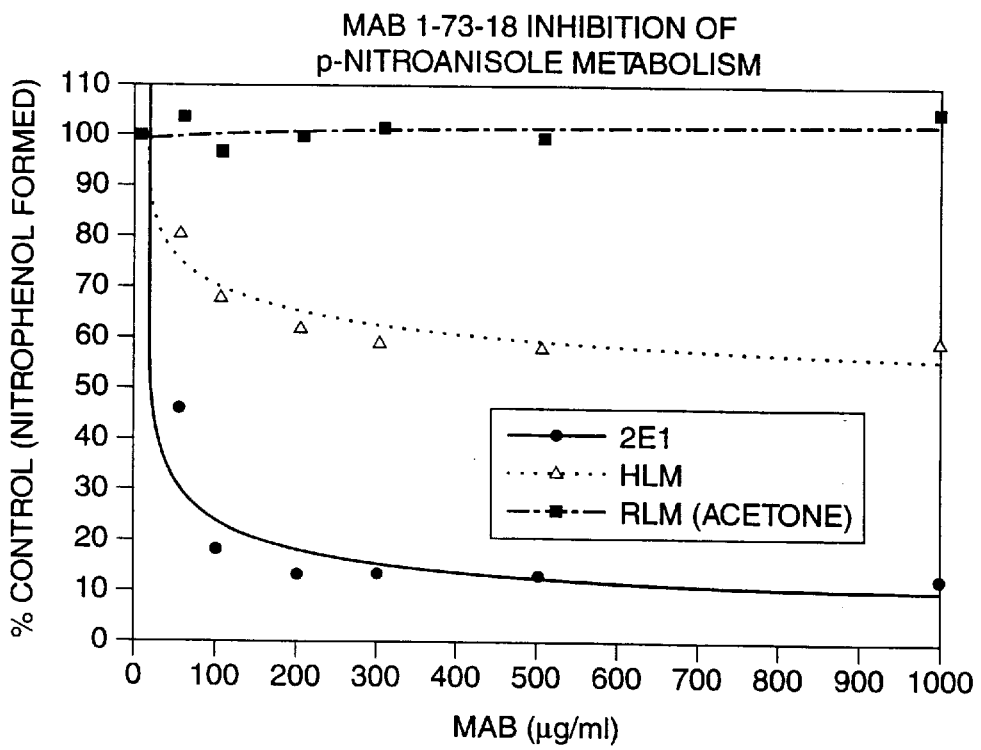
FIG. 9 shows monoclonal antibody 1-73-18 inhibition of p-nitroanisole metabolism. Monoclonal antibody 1-73-18 was preincubated with 2E1, HLM or acetone-induced RLM in MKPi for 5 min at 37° C. p-nitroanisole and 1 mM NADPH were added and incubated for 20 minutes. Monoclonal antibody 1-68-11 against rat 2C11 was employed as a control. The reaction was terminated with four volumes of dichloromethane, and deuterated nitrophenol was added as an internal standard. Extracts were derivatized with BSA and analyzed by GC-MS. Percentage of control was calculated as described with respect to FIG. 7.

FIG. 9 shows monoclonal antibody 1-73-18 inhibition of p-nitroanisole metabolism by human 2E1, human liver microsomes, or acetone-induced rat liver microsomes. The 2E1-catalyzed reaction was inhibited by 88%. Metabolism of p-nitroanisole by human liver microsomes was inhibited only by 40%, indicative of a relatively high contribution of the other P450s to the metabolism of p-nitroanisole. 1-73-18 does not inhibit p-nitroanisole metabolism by acetone-induced rat liver microsomes.

Figure 10:
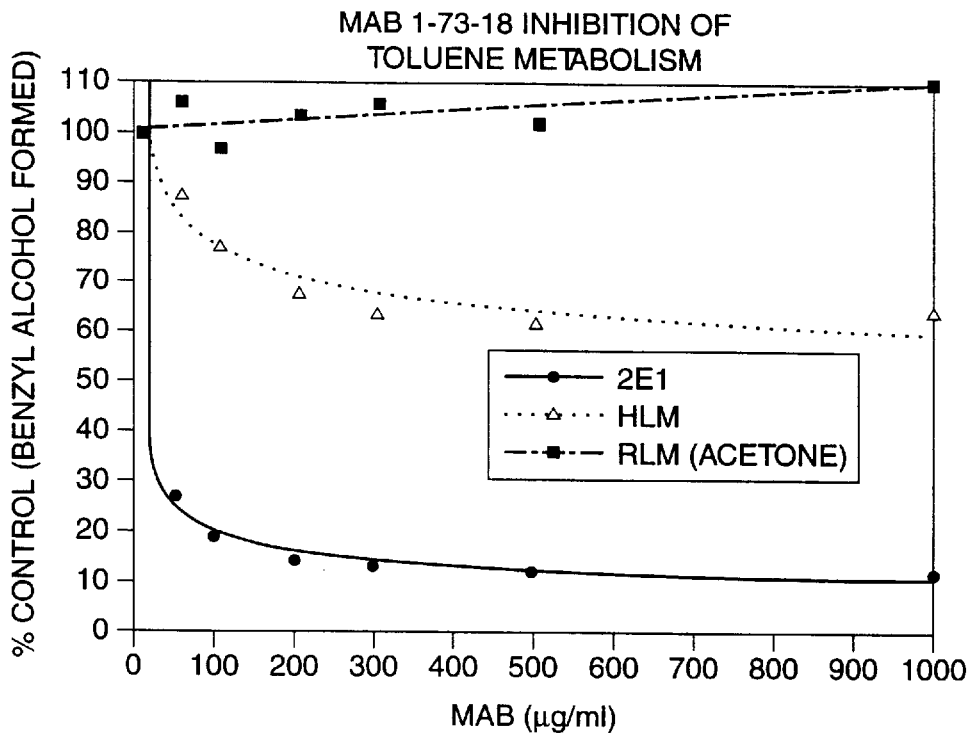
FIG. 10 shows monoclonal antibody 1-73-18 inhibition of toluene metabolism. Monoclonal antibody 1-73-18 was preincubated with 2E1, HLM or acetone-induced RLM in KPi for 5 min at 37° C. Toluene and NADPH were added in 1 ml final volume and incubated for 20 minutes. Monoclonal antibody 1-68-11 against rat 2C11 was used as a control. The reaction was terminated with dichloromethane and deuterated benzyl alcohol was used as an internal standard. Extracts were derivatized with BSA and analyzed by GC-MS. Percentage of control was calculated as described in the figure legend for FIG. 7.

Toluene is considered an enviromental pollutant and its methyl group is hydroxylated by P450 to produce benzyl alcohol. See Patten et al. *Arch. Biochem. Biophys.* 504 (1995), and Nakajima et al., *Int'l J. Biochem.* 1333 (1994). The turnover of toluene to benzyl alcohol was 22.4 (nmol/min) for human 2E1, 2.4 for human liver microsomes, and 13.9 for acetone-induced rat liver microsomes. As shown in FIG. 10, monoclonal antibody 1-73-18 inhibited the formation of benzyl alcohol catalyzed by 2E1 by 89%. Catalytic activity by human liver microsomes was inhibited by monoclonal antibody 1-73-18 by 38%. The liver microsomes from acetone-induced rats were resistant to the inhibition of toluene metabolism by monoclonal antibody 1-73-18.

Figure 11:
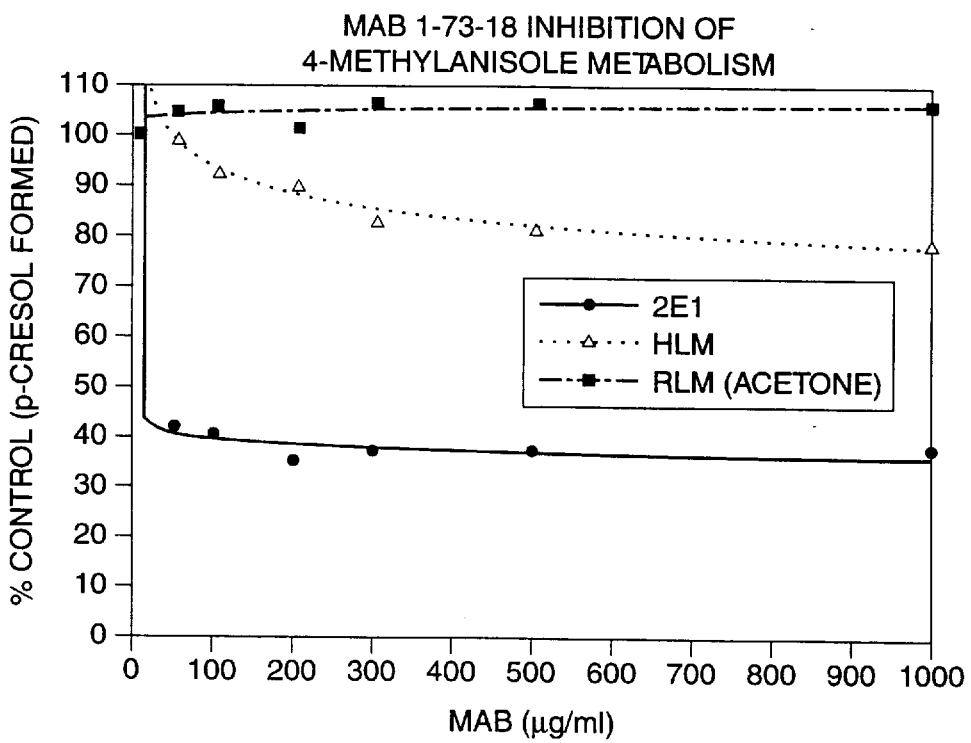
FIGS. 11 and 12 show monoclonal antibody 1-73-18 inhibition of 4-methylanisole metabolism. Monoclonal antibody 1-73-18 was preincubated with 2E1, HLM or acetone-induced RLM in 50 mM KPi for 5 min at 37° C. Toluene and NADPH were added and incubated for 20 minutes. Monoclonal antibody 1-68-11 against rat 2C11 was used as a control. The reaction was terminated with dichloromethane and deuterated benzyl alcohol was used as an internal standard. Extracts were derivatized with BSA and analyzed by GC-MS. Percentage of control was calculated as described in the description of FIG. 7.
Figure 12:
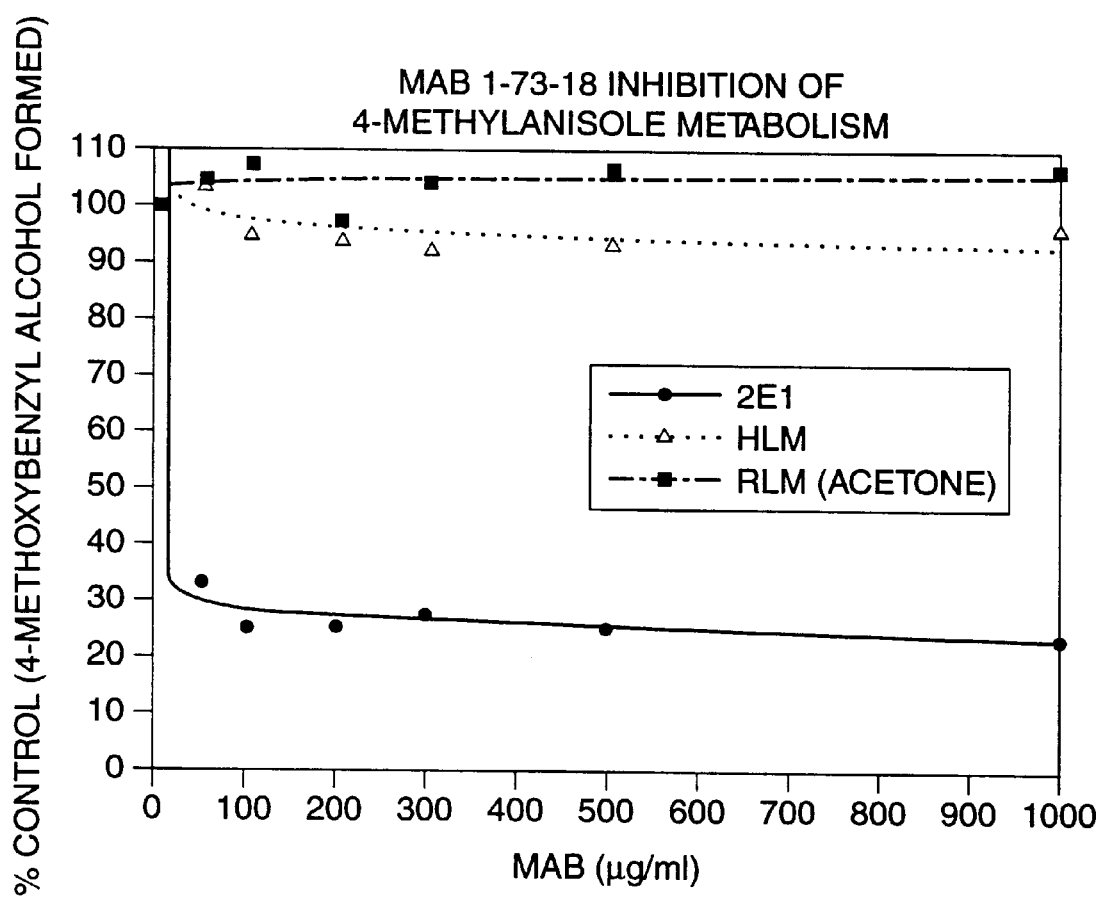

The inhibition of metabolism of 4-methylanisole to its metabolites, (p-cresole and 4-methoxybenzylalcohol) by monoclonal antibody 1-73-18 presented in FIGS. 11 and 12. The metabolism of 4-methylanisole by 2E1 to p-cresole was inhibited by 62% by 1-73-18 and the metabolism of 4-methylanisole to 4-methoxybenzylalcohol was inhibited by 77% by 1-73-18. But monoclonal antibody 1-73-18 did not significantly inhibit 2E1-catalyzed metabolism by either human liver microsomes or acetone-induced rat liver microsomes.

What is claimed is:

1. A monoclonal antibody or fragment thereof that specifically binds to human cytochrome P450 3A3, 3A4 and 3A5 at the same epitope as monoclonal antibody 3-29-9, ATCC NO: 97337, lacks specific binding to rat cytochrome P450 3A1, and that specifically inhibits the enzyme activity of human cytochrome P450 3A3, 3A4 and 3A5.

2. The monoclonal antibody or fragment of claim 1, which is a Fab fragment.

3. The monoclonal antibody or fragment according to claim 1 which is monoclonal antibody 3-29-9, ATCC NO: 97337.

4. The monoclonal antibody or fragment according to claim 1 which is a single chain antibody.

5. A monoclonal antibody or fragment thereof that specifically binds to human cytochrome P450 3A3 and 3A4 at the same epitope as monoclonal antibody 275-1-2, ATCC NO: 97338, without specifically binding to human cytochrome P450 3A5.

6. The monoclonal antibody or fragment of claim 5 that is a Fab fragment.

7. The monoclonal antibody or fragment according to claim 5 which is monoclonal antibody 275-1-2, ATCC NO: 97338.

8. The monoclonal antibody or fragment according to claim 5 which is a single chain antibody.

9. A monoclonal antibody or a fragment thereof which specifically binds to human cytochrome P450 2E1 at the same epitope as monoclonal antibody 1-73-18, ATCC NO: 97339 and lacks specific binding to acetone-treated rat microsomes, and specifically inhibits the enzyme activity of human cytochrome P450 2E1.

10. The monoclonal antibody or fragment of claim 9 that is a Fab fragment.

11. The monoclonal antibody or fragment of claim 9 which is monoclonal antibody 1-73-18, ATCC NO: 97339.

12. The monoclonal antibody or fragment of claim 9 which is a single chain antibody.

13. Monoclonal antibody 2-106-12, ATCC NO: 97340, or a fragment thereof, which binds to human cytochrome P450 2E1 in a Western blot.

14. The monoclonal antibody or fragment of claim 13, which is a single chain antibody.

* * * * *